US009267889B1

(12) United States Patent
Klopfer et al.

(10) Patent No.: US 9,267,889 B1
(45) Date of Patent: Feb. 23, 2016

(54) HIGH EFFICIENCY LIGHT ABSORBING AND LIGHT EMITTING NANOSTRUCTURES

(71) Applicant: STC.UNM, Albuquerque, NM (US)

(72) Inventors: Mike Klopfer, Albuquerque, NM (US); Ravinder Jain, Albuquerque, NM (US)

(73) Assignee: STC.UNM, Albuquerque, NM (US)

( * ) Notice: Subject to any disclaimer, the term of this patent is extended or adjusted under 35 U.S.C. 154(b) by 324 days.

(21) Appl. No.: 13/651,166

(22) Filed: Oct. 12, 2012

Related U.S. Application Data

(60) Provisional application No. 61/546,326, filed on Oct. 12, 2011.

(51) Int. Cl.
*H01J 61/00* (2006.01)
*G01N 21/64* (2006.01)

(52) U.S. Cl.
CPC .................................. *G01N 21/6428* (2013.01)

(58) Field of Classification Search
CPC ............ G01N 21/6428; G01N 21/554; G01N 2021/554; G01N 27/127; G01N 27/4146; G01N 33/54346; B82Y 30/00; B82Y 5/00
USPC ...................... 250/459.1, 492.1, 492.3, 336.1; 424/490; 977/932, 931, 948, 949, 950, 977/953, 954
See application file for complete search history.

(56) References Cited

U.S. PATENT DOCUMENTS

| 6,344,272 | B1 * | 2/2002 | Oldenburg et al. | 428/403 |
|---|---|---|---|---|
| 6,699,724 | B1 * | 3/2004 | West et al. | 436/525 |
| 6,924,921 | B2 * | 8/2005 | Lewis et al. | 359/296 |
| 7,147,687 | B2 * | 12/2006 | Mirkin et al. | 75/343 |
| 7,604,523 | B1 * | 10/2009 | Wedding et al. | 445/23 |
| 8,045,152 | B2 | 10/2011 | Halas et al. | |
| 8,067,737 | B1 * | 11/2011 | Sayyah | 250/336.1 |
| 8,376,013 | B2 * | 2/2013 | Bourke et al. | 156/379.6 |
| 8,409,863 | B2 * | 4/2013 | Natan et al. | 436/79 |
| 8,927,615 | B2 * | 1/2015 | Bourke et al. | 522/4 |
| 2002/0103517 | A1 * | 8/2002 | West et al. | 607/88 |
| 2002/0127224 | A1 * | 9/2002 | Chen | 424/130.1 |
| 2003/0082237 | A1 * | 5/2003 | Cha et al. | 424/490 |
| 2004/0229039 | A1 * | 11/2004 | Wei et al. | 428/403 |
| 2005/0058603 | A1 * | 3/2005 | Gao et al. | 424/9.32 |
| 2005/0158390 | A1 * | 7/2005 | Rana et al. | 424/489 |
| 2006/0102224 | A1 * | 5/2006 | Chen et al. | 136/203 |
| 2007/0059705 | A1 * | 3/2007 | Lu et al. | 435/6 |
| 2007/0218049 | A1 * | 9/2007 | Chen et al. | 424/130.1 |
| 2007/0292495 | A1 * | 12/2007 | Ludwig et al. | 424/450 |

(Continued)

OTHER PUBLICATIONS

Averitt, R. D., et al., "Plasmon resonance shifts of Au-Coated Au$_2$S nanoshells: Insight into multicomponent nanoparticle growth", *Physical Review Letters*, 78(22), (1997), 4217-4220.

(Continued)

*Primary Examiner* — David Porta
*Assistant Examiner* — Djura Malevic
(74) *Attorney, Agent, or Firm* — Schwegman Lundberg & Woessner, P.A.

(57) ABSTRACT

Apparatus, systems, and methods using multi-shelled nanostructures can be used in a variety of applications. In various embodiments, a multi-shelled nanostructure can include one or more light-absorbing and light-emitting cores enclosed by a number of nanoshells. For a multi-shelled nanostructure having multiple conductive nanoshells, the nanoshells are separated from each other by a dielectric. Additional apparatus, systems, and methods are disclosed.

45 Claims, 14 Drawing Sheets

(56) References Cited

U.S. PATENT DOCUMENTS

| | | | |
|---|---|---|---|
| 2008/0241262 A1* | 10/2008 | Lee et al. | 424/490 |
| 2009/0016962 A1* | 1/2009 | Fukumura et al. | 424/9.1 |
| 2009/0101838 A1* | 4/2009 | Boyden et al. | 250/459.1 |
| 2009/0213369 A1* | 8/2009 | Lee et al. | 356/301 |
| 2010/0009338 A1* | 1/2010 | Zhang et al. | 435/5 |
| 2010/0016783 A1* | 1/2010 | Bourke et al. | 604/20 |
| 2010/0224821 A1* | 9/2010 | Mandelbaum et al. | 252/62.53 |
| 2010/0261263 A1* | 10/2010 | Vo-Dinh et al. | 435/287.1 |
| 2010/0330147 A1* | 12/2010 | Hossainy et al. | 424/426 |
| 2011/0021970 A1* | 1/2011 | Vo-Dinh et al. | 604/20 |
| 2011/0022148 A1* | 1/2011 | Ruane et al. | 623/1.1 |
| 2011/0117202 A1* | 5/2011 | Bourke et al. | 424/490 |
| 2011/0126889 A1* | 6/2011 | Bourke et al. | 136/253 |
| 2011/0129537 A1* | 6/2011 | Vo-Dinh et al. | 424/490 |
| 2011/0275061 A1* | 11/2011 | Weidemaier et al. | 435/6.1 |
| 2012/0057165 A1* | 3/2012 | Natan et al. | 356/445 |
| 2012/0064134 A1* | 3/2012 | Bourke et al. | 424/401 |
| 2012/0212733 A1* | 8/2012 | Kodali et al. | 356/301 |
| 2012/0237447 A1* | 9/2012 | Lee et al. | 424/9.1 |
| 2013/0224282 A1* | 8/2013 | Wong et al. | 424/450 |
| 2014/0055845 A1* | 2/2014 | Jain | 359/344 |
| 2014/0199229 A1* | 7/2014 | Strano et al. | 423/447.2 |

OTHER PUBLICATIONS

Cai, W. B, et al., "Nanoplatforms for targeted molecular imaging in living subjects", *Small*, 3(11), (2007), 1840-1854.

Enderlein, J., "Spectral properties of a fluorescing molecule within a spherical metallic nanocavity", *Phys. Chem. Chem. Phys.*, 4, (2002), 2780-2786.

Hovel, M., et al., "Dielectric properties of ultrathin metal films around the percolation threshold", *Physical Review B* 81, (2010), 035402-1-035402-8.

Jackson, J. B., et al., "Controlling the surface enhanced raman effect via the nanoshell geometry", *Applied Physics Letters*, 82(2), (2003), 257-259.

Jin, Yongdong, et al., "Plasmonic fluorescent quantum dots", *Nature Nanotechnolgy—Letters*, vol. 4, (Sep. 2009), 571-576.

Kerker, M., et al., "Elastic scattering, absorption, and surface-enhanced Raman scattering by concentric spheres comprised of a metallic and a dielectric region", *Physical Review B*, 26(8), (1982), 4052-4063.

Kim, Jun-Hyun, et al., "Preparation, characterization, and optical properties of gold, silver, and Gold—Silver alloy nanoshells having silica cores". *Langmuir*, 24, (2008), 11147-11152.

Klopfer, M., et al., "Plasmonic quantum dots for nonlinear optical applications [Invited]", *Optical Materials Express*, 1(7), (2011), 1353-1366.

Kodali, Anil K.., et al., "Optimally designed nanolayered metal-dielectric particles as probes for massively multiplexed and ultrasensitive molecular assays", *Proc. Natl. Acad. Sciences USA*, 107(31), (Aug. 2010), 13620-13625.

Koole, R., et al., "On the Incorporation Mechanism of Hydrophobic Quantum Dots in Silica Spheres by a Reverse Microemulsion Method", *Chem. Mater.*, .20(7), (2008), 2503-2512.

Kraus, W. A., et al., "Plasmon resonance broadening in small metal particles", *The Journal of Chemical Physics*, 79, (1983), 6130-6139.

Larson, D. R., et al., "Water-Soluble quantum dots for multiphoton fluorescence imaging in vivo", *Science* 300, (2003), 1434-1436.

Leru, Eric C., et al., "Principles of Surface-Enhanced Raman Spectroscopy and related plasmonic effects", (2009), 15 pgs.

Liaw, Jiunn-Woie, et al., "Plasmonic effect of nanoshelled nanocavity on encapsulated emitter's spontaneous emission", *Journal of Quantitative Spectroscopy and Radiative Transfer*, 112, (2001), 2480-2485.

Miao, X., et al., "Nanocomposite plasmonic fluorescence emitters with core/shell configurations", *J. Opt. Soc. Am. B*. 27(8), (Aug. 2010), 1561-1570.

Moroz, A., "Electron mean free path in a spherical shell geometry", *The Journal of Physical Chemistry C*, 112, (2008), 10641-10652.

Neeves, A. E., et al., "Composite structures for the enhancement of nonlinear-optical susceptibility", *Journal of the Optical Society of America B*, 6(4), (Apr. 1989), 787-796.

Norton, Stephen J., et al., "Plasmonics quenching and enhancement of a fluorescing molecule outside and inside a silver metallic nanoshell", *IEEE Transactions on Nanotechnology*, 10(6), (Nov. 2011), 1264-1274.

O'Neal, D. Patrick, et al., "Photo-thermal tumor ablation in mice using near infrared-absorbing nanoparticles", *Cancer Letters*, 209, (2004), 171-176.

Oldenburg, S, J., et al., "Nanoengineering of optical resonances", *Chemical Physics Letters*, 288, (May 22, 1998), 243-247.

Oldenburg, S. J., et al., "Surface enhanced raman scattering in the near infrared using metal nanoshell substrates". *The Journal of Chemical Physics*, 111(10), (1999), 4729-4735.

Prodan, E., et al., "A hybridization model for the plasmon response of complex nanostructures", *Science*. vol. 302, (Oct. 2003), 419-422.

Qi, Zu-De, et al., "Biocompatible CdSe quantum dot-based photosensitizer under two-photon excitation for photodynamic therapy", *Journal of Materials Chemistry*, 21, (2011), 2455-2458.

Rasch, Michael R., et al., "Limitations on the optical tunability of small diameter gold nanoshells", *Langmuir*, 25(19), (2009), 11777-11785.

Raschke, G., et al., "Gold nanoshells improve single nanoparticle molecular sensors", *Nano Letters*, 4(10), (2004), 1853-1857.

Wang, L., et al., "Enhancement of Two-Photon Absorption-Induced Florescence in Semiconductor Quantum Dots by Gold Nanoparticles", (Paper NME4), *Nonlinear Optics: Materials Fundamentals and Applications in Proceedings Advances in Optical Sciences Congress*, (2009), 3 pgs.

Wang, L., "Nonlinear optics in quantum-confined and surface-plasmon structures", Dissertation, University of New Mexico, https://repository.unm.edu/handle/1928/10916, (May 2010), 108 pgs.

Wang, Xuefeng F., et al., "Refractive index and dielectric constant evolution of ultra-thin gold from clusters to film", *Optics Express*, vol. 18, No. 24, (2010), 24859-24867.

Xia, et al., "Engineering sub-100 nm multi-layer nanoshells", *Nanotechnology* 17, (2006), 5435-5440.

Xu, Hongxing, "Multilayered metal core-shell nanostructures for inducing a large and tunable local optical field", *Physical Review B* 72, (2005), 073405-1-073405-4.

Yaghini. E., et al., "Quantum dots and their potential biomedical applications in photosensitization for photodynamic therapy", *Nanomedicine*, 4, (2009), 353-363.

* cited by examiner

HIGH EFFICIENCY LIGHT ABSORBING AND LIGHT EMITTING NANOSTRUCTURES

RELATED APPLICATION

This application claims priority and the benefit under 35 U.S.C. 119(e) of U.S. Provisional Application Ser. No. 61/546,326, filed 12 Oct. 2011, which application is incorporated herein by reference in its entirety.

GOVERNMENT INTEREST STATEMENT

This invention was made with Government support under Grant No. USAF/AFOSR FA9550-09-1-0202 and Grant No. USAF/AFOSR FA9550-10-1-0252. The United States Government has certain rights in the invention.

FIELD OF THE INVENTION

This invention relates generally to higher efficiency light absorbing and light emitting nanostructures and their applications.

BACKGROUND

High-efficiency light absorbing and emitting nanostructures are critically needed for a large range of opto-electronic devices and systems applications, ranging from solar cells and simple detectors to advanced light emitter-based applications, including those based on multiphoton light absorption. As a case in point, two-photon absorption-induced fluorescence (TPAF) has been demonstrated as a powerful nonlinear optical phenomenon for several bio-imaging applications, particularly for deep-tissue imaging and for photodynamic therapy. In photodynamic therapy, the photon generated by two-photon upconversion is used to generate cytotoxic reactive oxygen species (ROS) in cancer tissue. Focusing intense near-infrared radiation (NIR) in cancer tissue that is relatively transparent to the NIR, whose wavelength is in the tissue optical transparency window of 600-1300 nm, can result in deep tissue penetration followed by selective destruction of malignant cells via efficient TPAF-induced ROS generation. Additional targeting of specific tissue can also be achieved by functionalizing the TPAF nanoparticles with biomolecules to cause increased accumulation in the target tissue, both for photodynamic therapy and for imaging applications.

Modeling of nanostructures can include analysis using the permittivities of materials assumed to be part of the nanostructures being modeled. In such modeling, the bulk dielectric constants of the materials may be typically used. However, there are some recent experimental efforts at measuring the permittivity of ultra thin layers of noble metals. In two articles, the measured permittivity for gold films from 2-10 nm thick on a silica substrate was reported. In an article, the use of picometrology was reported with measurements at 532 nm and 488 nm wavelengths, which are not useful for TPAF in most tissues. The use of ellipsometry to determine the complex relative dielectric constant for wavelengths from 280 nm to 1.7 μm has been reported. For 800 nm, the results of measurements of the real relative dielectric constant in the range (−20, 17) and imaginary relative dielectric constant in the range (2, 30) for gold thicknesses from 3-10 nm have been reported. See, for example, M. Hovel, B. Gompf, and M. Dressel, "Dielectric properties of ultrathin metal films around the percolation threshold," Phys. Rev. B 81, 035402 (2010), and X. Wang, K. Chen, M. Zhao, and D. D. Nolte, "Refractive index and dielectric constant transition of ultra-thin gold from cluster to film," Opt. Express 18, 2485924867 (2010).

There has been a long-standing need for high-brightness, nonphotobleaching, and nontoxic TPAF fluorophores for numerous medical research and clinical applications. During the last decade, semiconductor quantum dots (QDs) have attracted significant attention as TPAF nanoparticle labels due to their significant advantages over other fluorophores, which include: (a) broad absorption spectra and readily tunable emission options (b) high quantum yields, (c) relatively high photochemical stability, and (d) relatively large two-photon absorption cross sections. Unfortunately, QDs frequently contain toxic elements (such as cadmium), which limits their use for in vivo clinical applications.

Studies of related subject matter have been reported in a number of articles. These articles include:

1. D. R. Larson, W. R. Zipfel, R. M. Williams, S. W. Clark, M. P. Bruchez, F. W. Wise, and W. W. Webb, "Water- Soluble quantum dots for multiphoton fluorescence imaging in vivo," Science 300, 1434-1436 (2003).

2. E. Yaghini, A. M. Seifalian, and A. J. MacRobert, "Quantum dots and their potential biomedical applications in photosensitization for photodynamic therapy," Nanomedicine 4, 353-363 (2009).

3. L. Wang, D. Ankuciwiez, J. Chen, and R. K. Jain, "Enhancement of Two-Photon Absorption-Induced florescence in semiconductor quantum dots by gold nanoparticles," in "Nonlinear Optics: Materials, Fundamentals and Applications," (Optical Society of America, 2009), p. NME4.

4. R. K. Jain, "Advanced plasmonic devices for optoelectronic and integrated plasmon-optic circuit applications," proposal submitted to AFOSR, University of New Mexico reference number UNM 235/1099 (2009).

5. L. Wang, "Nonlinear optics in quantum-confined and surface-plasmon structures," Dissertation, May 2010, Univ. of New Mexico, https://repository.umn.edu/handle/1928/10916 (2010). Electrical and Computer Engineering.

6. M. Kerker and C. G. Blatchford, "Elastic scattering, absorption, and surface-enhanced raman scattering by concentric spheres comprised of a metallic and a dielectric region," Physical Review B 26, 4052 (1982).

7. R. D. Averitt, D. Sarkar, and N. J. Halas, "Plasmon resonance shifts of Au-Coated Au 2S nanoshells: Insight into multicomponent nanoparticle growth," Physical Review Letters 78, 4217 (1997).

8. S. J. Oldenburg, S. L. Westcott, R. D. Averitt, and N. J. Halas, "Surface enhanced raman scattering in the near infrared using metal nanoshell substrates," The Journal of Chemical Physics 111, 4729 (1999).

9. J. Enderlein, "Spectral properties of a fluorescing molecule within a spherical metallic nanocavity," Phys. Chem. Chem. Phys. 4, no. 12 (5): 2780-2786 (2002).

10. D. O'Neal, L. R. Hirsch, N. J. Halas, J. Payne, and J. L. West, "Photo-thermal tumor ablation in mice using near infrared-absorbing nanoparticles," Cancer Letters 209, 171-176 (2004).

11. J. B. Jackson, S. L. Westcott, L. R. Hirsch, J. L. West, and N. J. Halas, "Controlling the surface enhanced raman effect via the nanoshell geometry," Applied Physics Letters 82, 257 (2003).

12. E. Prodan, C. Radloff, N. J. Halas, and P. Nordlander, "A hybridization model for the plasmon response of complex nanostructures," Science 302, 419-422 (2003).

13. H. Xu, "Multilayered metal core-shell nanostructures for inducing a large and tunable local optical field," Physical Review B 72, 073405 (2005).

14. X. Xia, Y. Liu, V. Backman, and G. A. Ameer, "Engineering sub -100 nm multi-layer nanoshells," Nanotechnology 17, 5435-5440 (2006).

15. A. K, Kodali, X. Llora, and R. Bhargava, "Optimally designed nanolayered metal-dielectric particles as probes for massively multiplexed and ultrasensitive molecular assays," Proceedings of the National Academy of Sciences (2010).

16. M. R. Rasch, K. V. Sokolov, and B. A. Korgel, "Limitations on the optical tunability of small diameter gold nanoshells," Langmuir 25, 11777-11785 (2009).

17. Y. Jin and X. Gao, "Plasmonic fluorescent quantum dots," Nat Nano 4, 571-576 (2009).

18. X. Miao, I. Brener, and T. S. Luk, "Nanocomposite plasmonic fluorescence emitters with core/shell configurations," Journal of the Optical Society of America B Optical Physics 27, 1561-1570 (2010).

19. J. Liaw and C. Liu, "Plasmonic effect of nanoshelled nanocavity on encapsulated emitter's spontaneous emission," Journal of Quantitative Spectroscopy and Radiative Transfer 112, 2480-2485 (2011), 20. S. J. Norton and T. Vo-Dinh, "Plasmonics quenching and enhancement of a fluorescing molecule outside and inside a silver metallic nanoshell," IEEE Transactions on Nanotechnology (2011).

21. E. L. Ru and P. Etchegoin, Principles of Surface-Enhanced Raman Spectroscopy: and related plasmonic effects (Elsevier Science, 2008), 1st ed.

22. M. Hovel, B. Gompf, and M. Dressel, "Dielectric properties of ultrathin metal films around the percolation threshold," Phys. Rev. B 81, 035402 (2010).

23. X. Wang, K. Chen, M. Zhao, and D. D. Nolte, "Refractive index and dielectric constant transition of ultra-thin gold from cluster to film," Opt. Express 18, 2485924867 (2010).

24. A. E. Neeves and M. H. Birnboim, "Composite structures for the enhancement of nonlinear-optical susceptibility," Journal of the Optical Society of America B 6, 787-796 (1989).

25. R. Koole, M. M. van Schooneveld, J. Hilhorst, C. de Mello Doneg, D. C. 't Hart, A. van Blaaderen, D. Vanmaekelbergh, and A. Meijerink, "On the incorporation mechanism of hydrophobic quantum dots in silica spheres by a reverse microemulsion method," Chemistry of Materials 20, 2503-2512 (2008).

26. J. Kim, W. W. Bryan, and T. R. Lee, "Preparation, characterization, and optical properties of gold, silver, and Gold-Silver alloy nanoshells having silica cores," Langmuir 24, 11147-11152 (2008).

27. A. Moroz, "Electron mean free path in a spherical shell geometry," The Journal of Physical Chemistry C 112, 10641-10652 (2008).

28. G. Raschke, S. Brogl, A. S. Susha, A. L. Rogach, T. A. Klar, J. Feldmann, B. Fieres, N. Petkov, T. Bein, A. Nichtl, and K. Krzinger, "Gold nanoshells improve single nanoparticle molecular sensors," Nano Letters 4, 1853-1857 (2004).

29. W. A. Kraus and G. C. Schatz, "Plasmon resonance broadening in small metal particles," The Journal of Chemical Physics 79, 6130 (1983).

30. Zu-De Qi, et al "Biocompatible CdSe quantum dot-based photosensitizer under two-photon excitation for photodynamic therapy, "J. Mater. Chem., 2011, 21, 2455-2458

All of the references listed above are incorporated herein by reference in their entirety.

BRIEF DESCRIPTION OF THE DRAWINGS

Embodiments of the invention are illustrated by way of example and not limitation in the figures of the accompanying drawings in which.

DETAILED DESCRIPTION

The following detailed description refers to the accompanying drawings that show, by way of illustration and not limitation, various example embodiments of the invention. These embodiments are described in sufficient detail to enable those skilled in the art to practice these and other embodiments. Other embodiments may be utilized, and structural, logical, and electrical changes may be made to these embodiments. The various embodiments are not necessarily mutually exclusive, as some embodiments can be combined with one or more other embodiments to form new embodiments. The following detailed description is, therefore, not to be taken in a limiting sense.

In various embodiments, nanoparticle-based absorbers and fluorophores can be provided for numerous high-efficiency absorber and emitter device applications. Emitter device applications can include the use of TPAF in such nanoparticles for medical applications such as deep-tissue imaging and deep-tissue photodynamic therapy (PDT). For example, plasmonic quantum dot nanoparticle assemblies can be used for such applications. The design of optimized nanostructures can be realized that result in enhancement of fluorescence signal intensity (and corresponding increases in PDT efficacies) by greater than a factor of 160,000 compared to those obtainable under comparable illumination conditions from the same fluorescent labels used without plasmonic enhancement. These fluorescent labels can include quantum dots or other light-absorbing and light-emitting structures.

In various embodiments, structures, which can provide for brighter nonlinear fluorophores, can include the use of "plasmonic QDs", namely QDs surrounded by one or more layers of insulators and metallic noble metal shells. Such structures can reduce toxicity. Using Mie theory, it can be shown analytically that significantly large field enhancements can be obtained, especially with multi-shell dielectric noble metal nanoparticle structures. These enhancements can be obtained using dielectrics with high permittivity, leading to TPAF signal enhancements of over 160,000. Designs for such structures may be based on an estimate of optimized dimensions for several multi-shell structures. As can analytically be shown, an improved field enhancement for multi-shell metal dielectric nanoparticles with QD core using a dielectric with higher permittivity compared to $SiO_2$ dielectric can be realized. The QD at the core of the nanostructures may decrease the field enhancement compared to the dielectric core without a QD at the core.

Figure 1:
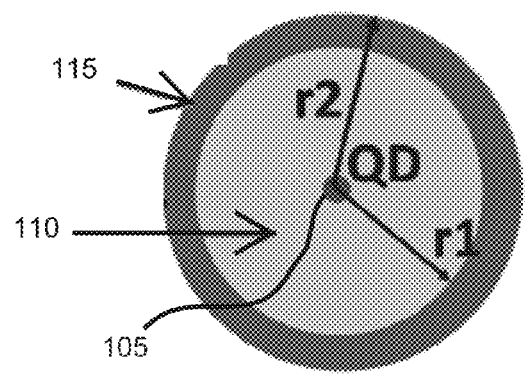
FIG. 1 schematically depicts a double-shelled plasmonic quantum dot nanostructure, in accordance with various embodiments.

FIG. 1 illustrates a plasmonic quantum dot (PQD) structure including a QD 105 enclosed by a low-loss high-index dielectric nanoshell 110, which is further enclosed by an ultrathin nanoshell 115 of a plasmonic noble metal. With respect to nanostructures, see co-pending patent application: "*Apparatus and Methods Using Non-Toxic Synthetic Luminophores*", U.S. patent application Ser. No. 13/099,217 filed May 2, 2011, which application is incorporated herein by reference. Gold is an example of a plasmonic noble metal. These nanoshells in appropriately designed and optimized PQD structures can help enhance the fields in the center of the nanostructure, thus increasing the brightness of the nanoparticles, and can chemically isolate the QDs from the tissue, which can significantly reduce the toxicity of these TPAF nanoparticles. A significant portion of previous research on the use of noble metal nanoshells and of their plasmonic properties has focused on properties such as location and shift of the plasma resonances, far-field optical properties such as absorption and extinction spectra, and field enhancements external to the metal nanoshell structures. In various embodiments, structures are arranged with respect to field enhancement inside the nanoparticle. Such structures can include designs that focus on optimization of the enhancement of the fields within quantum dot-dielectric shell-metallic nanoshell structures to enable the highest field enhancements at the location of the quantum dots near the center of the nanostructures, thereby enabling the design of ultrahigh brightness plasmonic quantum dot emitters. Such plasmonic quantum dot emitters can be used in TPAF applications.

In various embodiments, light emitters comprise one or more light-absorbing and light-emitting cores enclosed in an appropriate conductive nanoshell with an appropriate dielectric layer between the light-absorbing and light-emitting cores and the conductive nanoshell to minimize nonradiative decay and optimize plasmonic resonant enhancement. These emitters can be provided as high-brightness sources for a variety of applications. The conductive nanoshell may provide a single concentric structure, as shown schematically in FIG. 1. The one or more light-absorbing and light-emitting cores may comprise, but are not limited to, one or more QDs, The conductive nanoshell can be a metallic conductive shell, for example, but not limited to an appropriate gold nanoshell or an appropriate silver nanoshell. A model for use may assume nanoparticles (NPs) that contain a single semiconductor quantum dot core, a single dielectric "nanoshell" layer, and a single noble metal nanoshell layer, with these nanoparticles surrounded by water/aqueous tissue, as is ubiquitous in bio-imaging applications.

Vector spherical harmonics (VSH) can be used in a methodology to compute fields and electric field enhancements (EFE) for analysis of the EFE in multilayered nanostructures. The methodology can be applied to Mie scattering calculations. The layer number is denoted by l, where the first layer is the core and the largest layer number denotes the surrounding media. The electric and magnetic fields in each layer l can be expressed as sums of vector spherical harmonics as follows:

$$E^l = \sum_{n,m} \alpha_{nm}^l M_{nm}^{(1)}(k_l, r, \Omega) +$$

-continued $$H^l = \sum_{n,m} \alpha_{nm}^l k_l N_{nm}^{(1)}(k_l, r) + \delta_{nm}^l k_l N_{nm}^{(3)}(k_l, r) + \\ \delta_{nm}^l M_{nm}^{(3)}(k_l, r, \Omega) + \gamma_{nm}^l N_{nm}^{(1)}(k_l, r, \Omega) + \beta_{nm}^l N_{nm}^{(3)}(k_l, r, \Omega) \\ \gamma_{nm}^l k_l M_{nm}^{(1)}(k_l, r) + \beta_{nm}^l k_l M_{nm}^{(3)}(k_l, r)$$

where n is the angular momentum, and m is its projection onto the z axis. The unknown coefficients of the VSHs are denoted by $\alpha_{nm}^l, \beta_{nm}^l, \delta_{nm}^l, \gamma_{nm}^l$. The vector spherical harmonics are defined as:

$$M_{nm}^{(i)}(k, r, \Omega) = \nabla \times r\xi^{(i)}(k, r, \Omega)\hat{r}$$

$$N_{nm}^{(i)}(k, r, \Omega) = \frac{1}{k}\nabla \times M_{nm}^{(i)}(k, r, \Omega)$$

$$\xi^{(i)}(k, r, \Omega) = \frac{1}{\sqrt{n(n+1)}} z_n^{(i)}(kr) Y_{nm}(\Omega)$$

$$z_n^{(1)}(kr) = j(kr)$$

$$z_n^{(3)}(kr) = h^1(kr)$$

where j is the spherical Bessel function and $h^1$ is the spherical Hankel function of the first kind. The spherical coordinates are denoted by r, θ, φ, with $\Omega=(\theta,\phi)$, and the wavenumber is defined as $K=\sqrt{\epsilon}\omega/c$.

Integrating over the surface of a sphere leads to the following $$\iint M_{nm}^{(i)}(k,r,\Omega) \cdot N_{n'm'}^{(j)*}(k,r,\Omega) d\Omega = 0$$

$$\iint N_{nm}^{(i)}(k,r,\Omega) \cdot M_{n'm'}^{(j)*}(k,r,\Omega) d\Omega = 0 \; \forall m \neq m' \vee n \neq n'$$

and $$\iint M_{nm}^{(i)}(k,r,\Omega) \cdot N_{n'm'}^{(j)*}(k,r,\Omega) d\Omega = 0 \; \forall m \neq m' \vee n \neq n'$$

Define $\mathcal{R}_{nm}^l(r) = \alpha_{nm}^l M_{nm}^{(1)}(k_l,r,\Omega) + \delta_{nm}^l M_{nm}^{(3)}(k_l,r,\Omega)$, $\mathcal{Q}_{nm}^l(r) = \gamma_{nm}^l N_{nm}^{(1)}(k_l,r,\Omega) + \beta_{nm}^l N_{nm}^{(3)}(k_l,r,\Omega)$, $\mathcal{J}_{nm}^l(r) = \alpha_{nm}^l k_l N_{nm}^{(1)}(k_l,r,\Omega) + \delta_{nm}^l k_l N_{nm}^{(3)}(k_l,r,\Omega)$ and $\mathcal{T}_{nm}^l(r) = \gamma_{nm}^l k_l M_{nm}^{(1)}(k_l,r,\Omega) + \beta_{nm}^l k_l M_{nm}^{(3)}(k_l,r,\Omega)$.

Applying the above orthogonality relations to the continuity of the tangential electric and magnetic fields at each interface between layers, the following is obtained:

$$\mathcal{R}_{nm}^l(r_l) \times \hat{r} = \mathcal{R}_{nm}^{l+1}(r_l) \times \hat{r} \quad (1)$$

$$\mathcal{Q}_{nm}^l(r_l) \times \hat{r} = \mathcal{Q}_{nm}^{l+1}(r_l) \times \hat{r} \quad (2)$$

$$\mathcal{J}_{nm}^l(r_l) \times \hat{r} = \mathcal{J}_{nm}^{l+1}(r_l) \times \hat{r} \quad (3)$$

$$\mathcal{T}_{nm}^l(r_l) \times \hat{r} = \mathcal{T}_{nm}^{l+1}(r_l) \times \hat{r} \quad (4)$$

where $r_l$ is the radius at the interface between layer l and layer l+1.

For the core region (l=1) the electric and magnetic fields must be finite at the origin, therefore $\gamma_{nm}^l = \delta_{nm}^l = 0$. The coefficients of the spherical harmonics for the incident plane wave $E^i$ in the surrounding media are given by $$\delta_{nm} = \beta_{nm} = 0 \; \forall n,m$$

$$\alpha_{nm} = \gamma_{nm} = 0 \; \forall |m| \neq 1$$

$$\alpha_{n1} = i^{n+1}\sqrt{\pi(2n+1)}$$

The scattered electromagnetic field $E^s$ must satisfy the radiation condition. Thus, it is of the form $$E^s = \sum_{n,m} \delta_{nm}^l M_{nm}^{(3)}(k_l, r, \Omega) + \beta_{nm}^l N_{nm}^{(3)}(k_l, r, \Omega)$$

There are two unknown coefficients at the core, two unknown coefficients in the outer media for the scattered field, and 4 unknown coefficients in each shell. Each interface between layers gives the four equations (1-4). These coefficients can be used to calculate $E^l(x)$ for any point, x in layer l. The EFE is given by the ratio $|E^l(x)|/|E^l|$.

Even though the analysis can be generalized to any semiconductor quantum dot material and size, consider TPA excitation of a 6 nm CdSe QD whose fluorescence peak occurs at a wavelength of approximately 600 nm, and whose optimum excitation wavelengths for TPA excitation lie in the 800 nm to 950 nm range. The approach above has ignored modifications to the bulk dielectric constants of noble metals, as nanoshells, caused by size-dependent and mean-free-path effects in the ultrathin shell thicknesses invoked in many of Mie scattering calculations and modifications in these dielectric constants due to limitations in fabrication of smooth and continuous ultrathin noble metal films.

The EFE for various dielectric permittivities and minimum bounds on layer thickness was investigated, in which it can be seen that the maximum EFE increases with minimum shell thickness. The maximum EFE for each permittivity and thickness bound was obtained using a gradient ascent search method and thus there is no guarantee that a global maximum was found. Excitation wavelengths of 800 nm and 950 nm are plotted, since both are in the tissue optical window, which allows observation of trends in EFE with wavelength. FIGS. 2-5 show plots for both gold and silver layers in the structure of FIG. 1.

Figure 2:
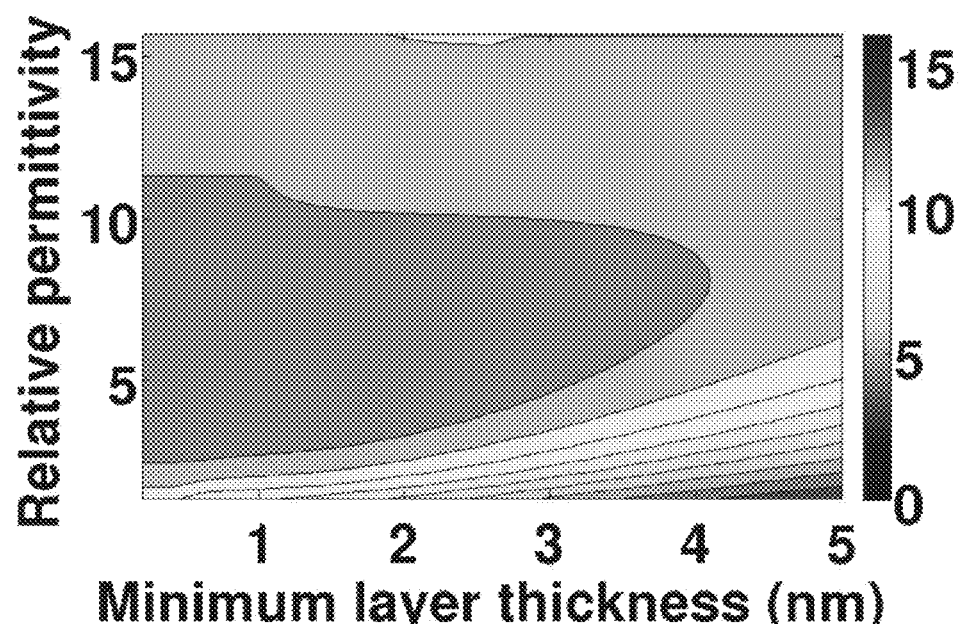
FIG. 2 shows electric field enhancements for silver modeled in the metal layers of the shelled nanoparticle in the structure of FIG. 1 at excitation wavelength 800 nm, in accordance with various embodiments.
Figure 3:
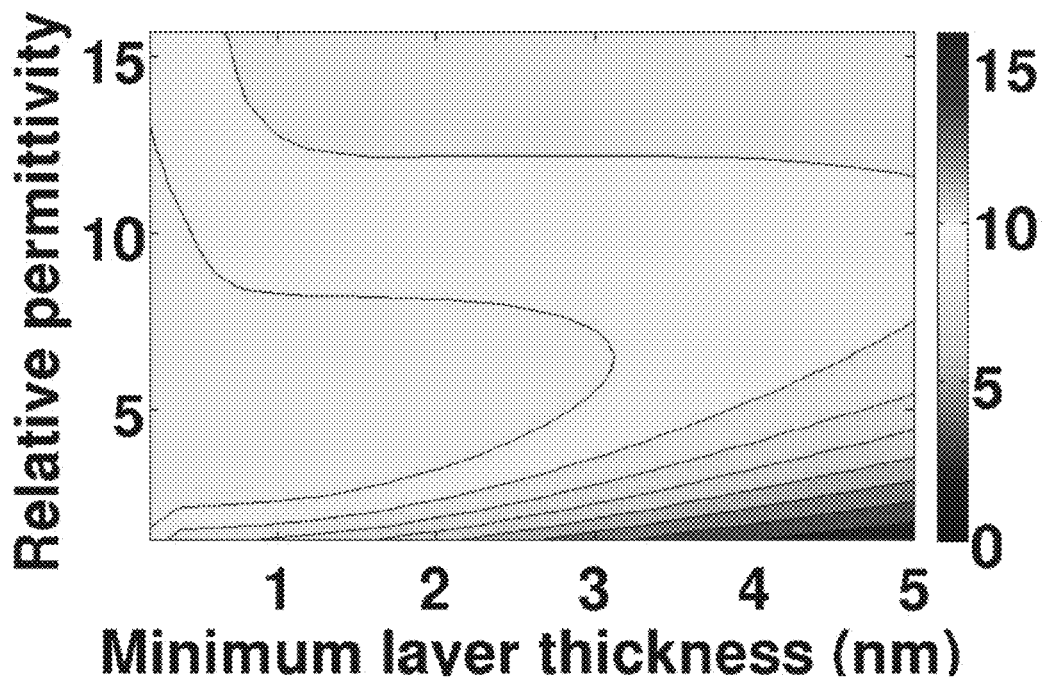
FIG. 3 shows electric field enhancements for silver modeled in the metal layers of the shelled nanoparticle in the structure of FIG. 1 at excitation wavelength 950 nm, in accordance with various embodiments.
Figure 4:
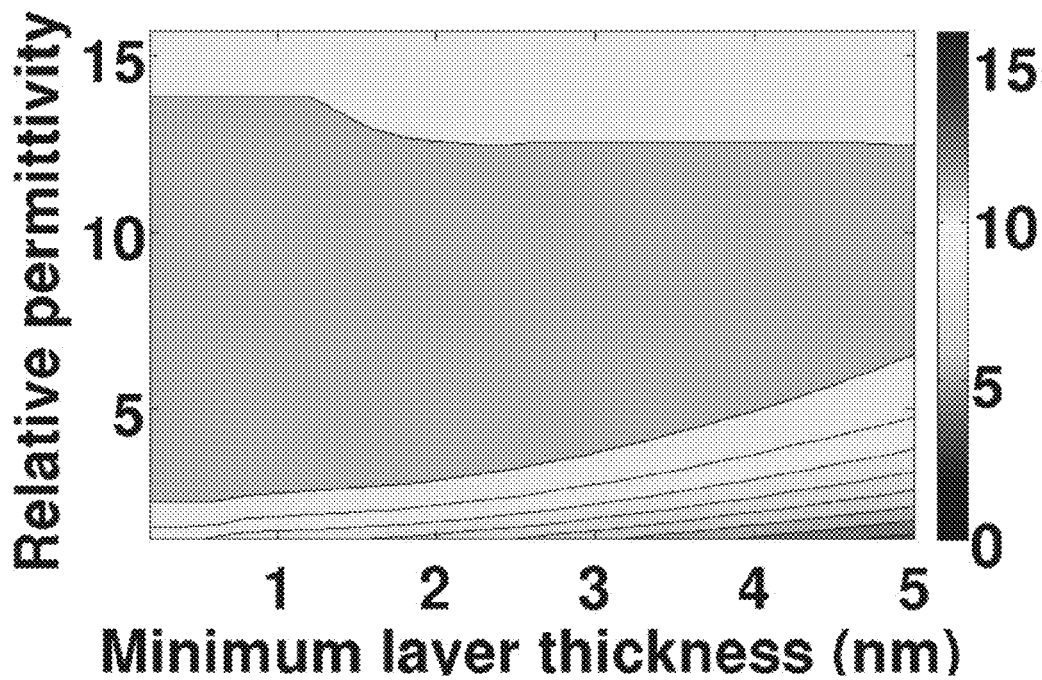
FIG. 4 shows electric field enhancements for gold modeled in the metal layers of the shelled nanoparticle in the structure of FIG. 1 at excitation wavelength 800 nm, in accordance with various embodiments.
Figure 5:
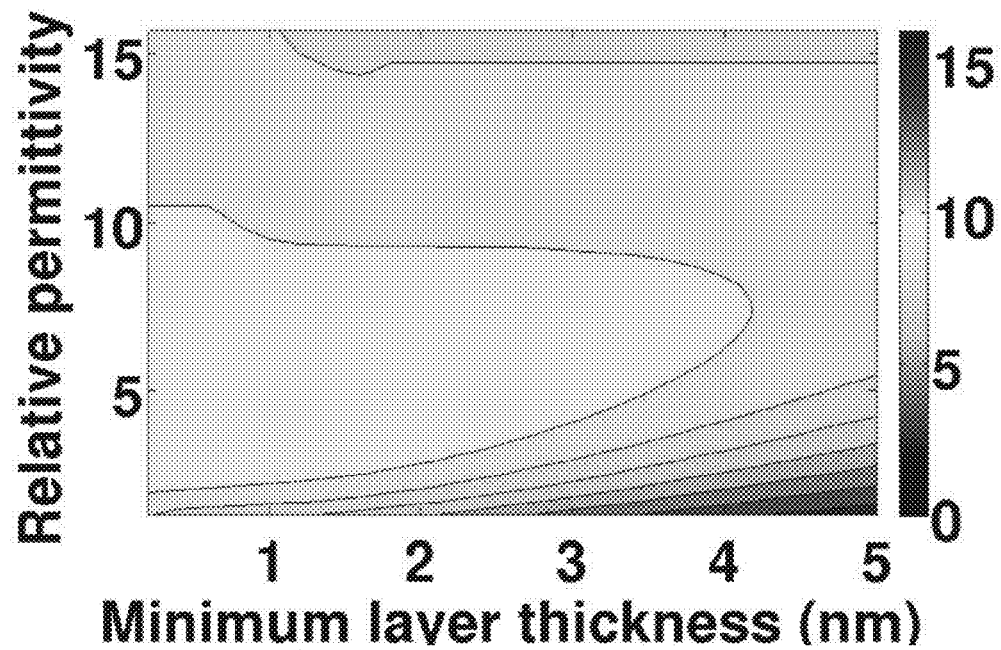
FIG. 5 shows electric field enhancements for gold modeled in the metal layers of the shelled nanoparticle in the structure of FIG. 1 at excitation wavelength 950 nm, in accordance with various embodiments.

FIG. 2 shows electric field enhancements for silver modeled in the metal layers of the shelled nanoparticle in the structure of FIG. 1 at excitation wavelength 800 nm. FIG. 3 shows electric field enhancements for silver modeled in the metal layers of the shelled nanoparticle in the structure of FIG. 1 at excitation wavelength 950 nm. FIG. 4 shows electric field enhancements for gold modeled in the metal layers of the shelled nanoparticle in the structure of FIG. 1 at excitation wavelength 800 nm. FIG. 5 shows electric field enhancements for gold modeled in the metal layers of the shelled nanoparticle in the structure of FIG. 1 at excitation wavelength 950 nm.

Figure 6:
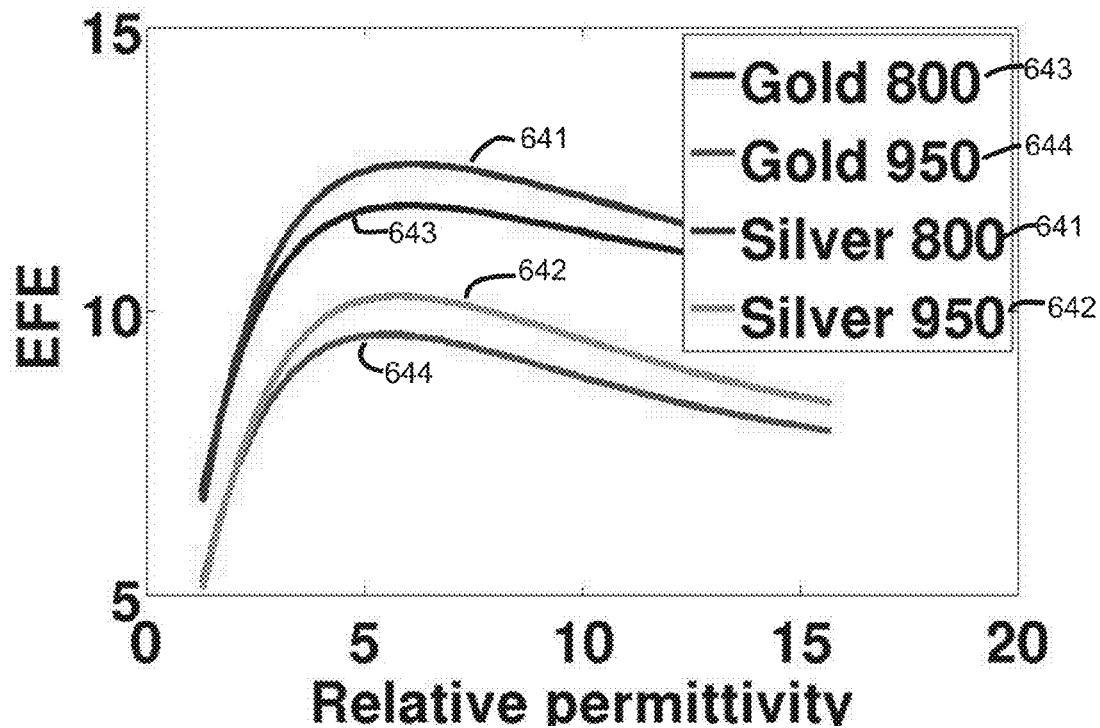
FIG. 6 shows electric field enhancements as a function of relative permittivity for each of gold and silver modeled in the metal layers of the shelled nanoparticle in the structure of FIG. 1 for a selected minimum layer thickness, in accordance with various embodiments.

FIG. 6 shows electric field enhancements as a function of relative permittivity for each of gold and silver modeled in the metal layers of the shelled nanoparticle in the structure of FIG. 1 for a 2.6 nm minimum layer thickness. Curve 643 shows EFE for gold at excitation wavelength 800 nm. Curve 644 shows EFE for gold at excitation wavelength 950 nm. Curve 641 shows EFE for silver at excitation wavelength 800 nm. Curve 642 shows EFE for silver at excitation wavelength 950 nm.

From these plots in FIGS. 2-5 and the combined plot in FIG. 6, it is apparent that silver has increased EFE compared to gold and that excitation at 800 nm has higher EFE than at 950 nm. In addition, EFE increases with smaller thickness bounds but does not increase monotonically with permittivity, as seen in FIG. 6.

Figure 7:
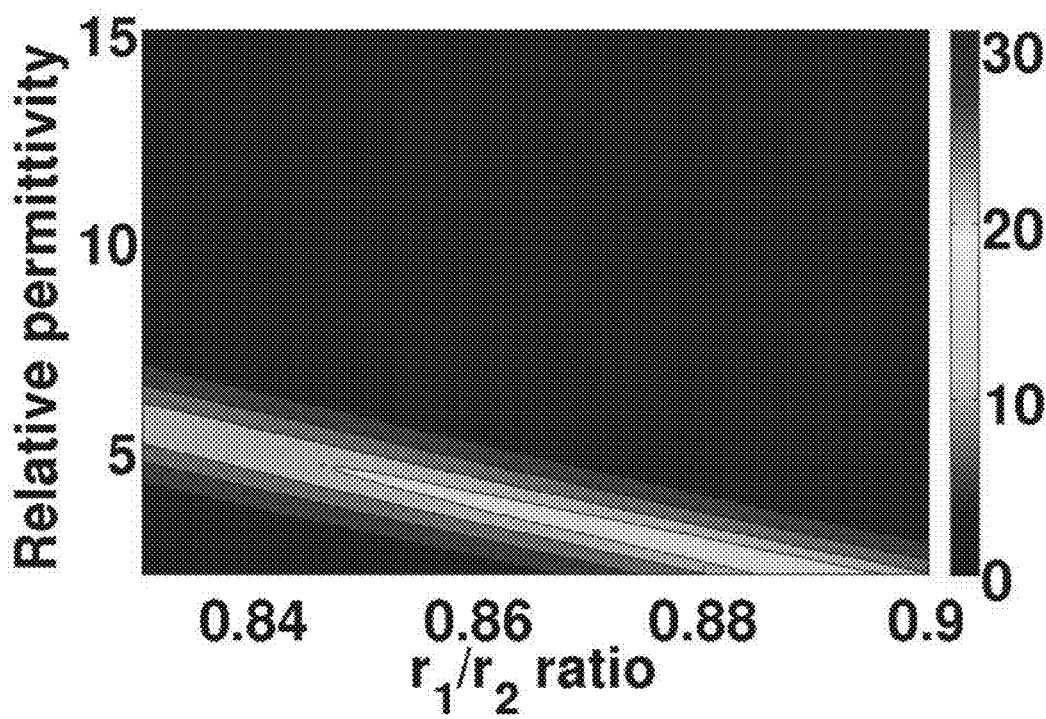
FIG. 7 shows quasistatic electric field enhancements of silica/gold nanoparticles for relative permittivity as a function of the ratio of the radius of the inner dielectric core and the outer radius of the metal shell of FIG. 1, in accordance with various embodiments.
Figure 8:
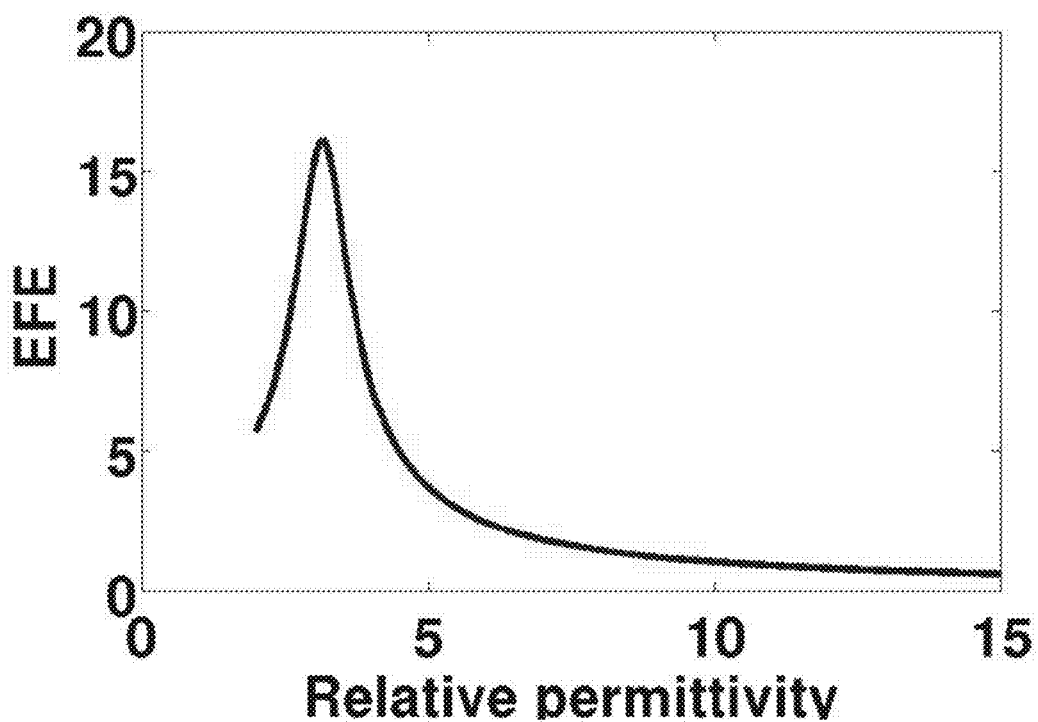
FIG. 8 shows the electric field enhancements for relative permittivity as a function of the ratio of the radius of the inner dielectric core and the outer radius of the metal shell of FIG. 1 equal to 0.86, in accordance with various embodiments.

To understand why the EFE doesn't increase monotonically with dielectric permittivity, consider the quasistatic approximation expression for a dielectric core, metal shell structure in a water medium using "Composite structures for the enhancement of nonlinear-optical susceptibility," A. E. Neeves and M. H. Birnboim, Journal of the Optical Society of America B 6, 787-796 (1989), which is incorporated by reference in its entirety. The following is an expression for the electric field intensity in the core:

$$E_1 = \frac{9\varepsilon_2\varepsilon_3}{\varepsilon_2\varepsilon_a + 2\varepsilon_3\varepsilon_b}E_0(\cos\theta\hat{r} - \sin\theta\hat{\theta})$$

where $\epsilon_a=\epsilon_1(3-2P)+2\epsilon_2P$, $\epsilon_b=\epsilon_1P+\epsilon_2(3-P)$, and $P=1-(r_1/r_2)^3$. The inner dielectric core has permittivity $\epsilon_1$ and radius $r_1$. The metal shell has permittivity $\epsilon_2$ and outer radius $r_2$. The permittivity of the water medium is denoted by $\epsilon_3$. The denominator, $\epsilon_2\epsilon_a+2\epsilon_3\epsilon_b$, is a linear function of the dielectric permittivity $\epsilon_1$. The denominator is complex, since the gold permittivity is complex. Therefore, the magnitude of the denominator has a minimum as a function of $\epsilon_1$, which is where $|E_1|$ attains a maximum for each value of the ratio $r_1/r_2$, as seen in FIG. 7. For the structure of FIG. 1 analyzed here, without a QD core, the maximum EFE increases for smaller dielectric permittivity. However, as seen in FIGS. 2-5, for the QD core case, the maximum EFE is attained for a relative dielectric permittivity of around 6, which is close to the 6.9 relative permittivity of the CdSe QD core in the modeled structure. FIG. 8 shows the electric field enhancements for relative permittivity as a function of the ratio of the radius of the inner dielectric core and the outer radius of the metal shell of FIG. 1 equal to 0.86.

Figure 9:
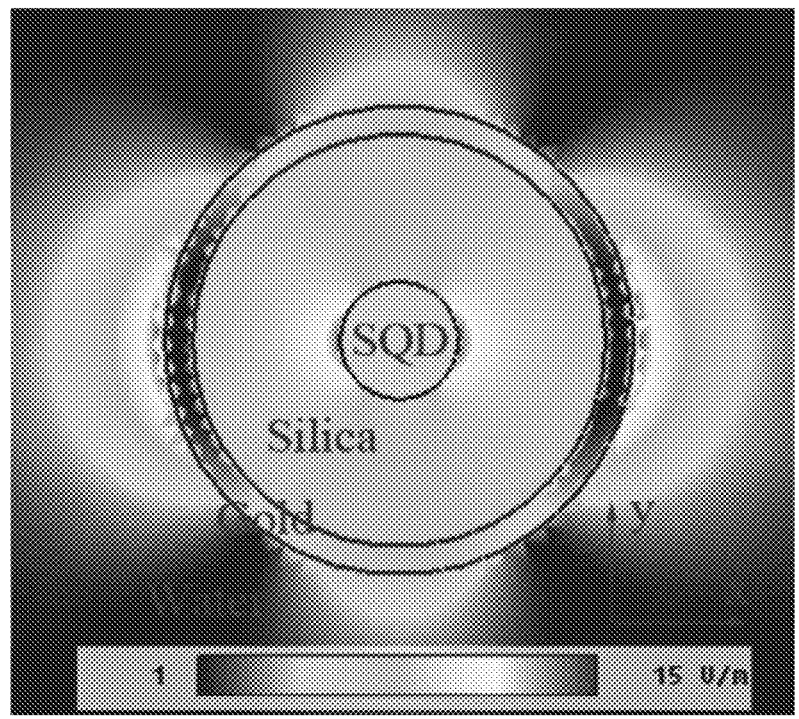
FIG. 9 shows a spatial plot of an electric field inside and outside of a single metal shell plasmonic quantum dot nanoparticle, in accordance with various embodiments.

FIG. 9 shows a spatial plot of an electric field inside and outside of a single shell plasmonic quantum dot nanoparticle, in accordance with various embodiments. The input field is 1 V/m, x-polarized. The nanoparticle has a CdSe SQD core and a gold nanoshell separated by silica, where the gold nanoshell has a 20 nm outer diameter and a 17.6 nm inner diameter with 1.2 nm thickness. FIG. 9 depicts strong electric field enhancement (EFE) factors (greater than 9) at the CdSe SQD, using 800 nm excitation.

In order to determine the effect of the quantum dot on the EFE, a comparison of a structure without a QD core with respect to a structure with a QD core was made. The structure without a QD core, labeled SA, was a silica shell/Au shell structure similar to FIG. 1 without the QD core, where the center of the silica shell is the effective silica core. The structure with a QD core, labeled QSA, was a OD/silica shell/Au shell structure. First, it was determined that the maximum field enhancement decreases with silica shell/core radius for SA structures. Secondly, it it was determined that the field enhancement in a QSA structure has decreased field enhancement in the QD compared to the field enhancement at the center of a SA nanoparticle. These structures were analyzed for an excitation wavelength of 800 nm.

Figure 10:
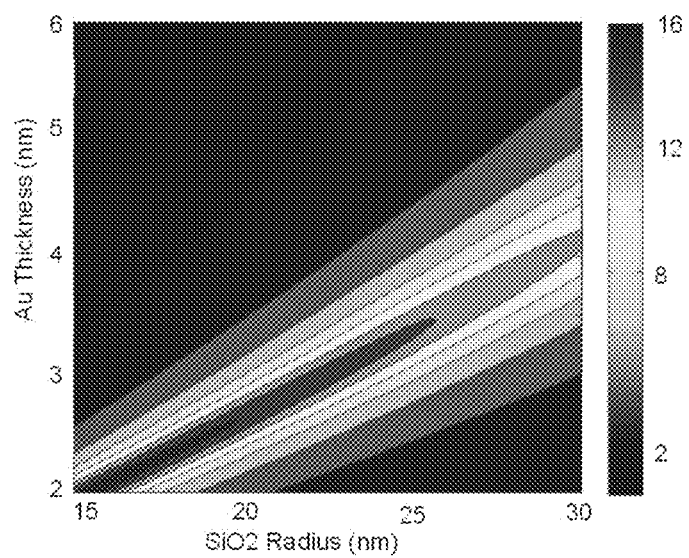
FIG. 10 shows the electric field enhancements at the center of a structure similar to FIG. 1 without a quantum dot core for various radii and thicknesses, in accordance with various embodiments.
Figure 11:
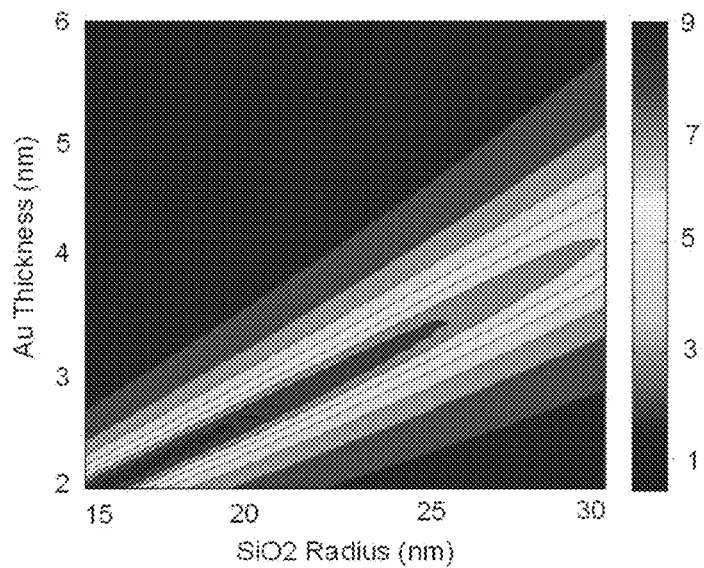
FIG. 11 shows the electric field enhancements at the center of a structure similar to FIG. 1 with a quantum dot core for various radii and thicknesses, in accordance with various embodiments.
Figure 12:
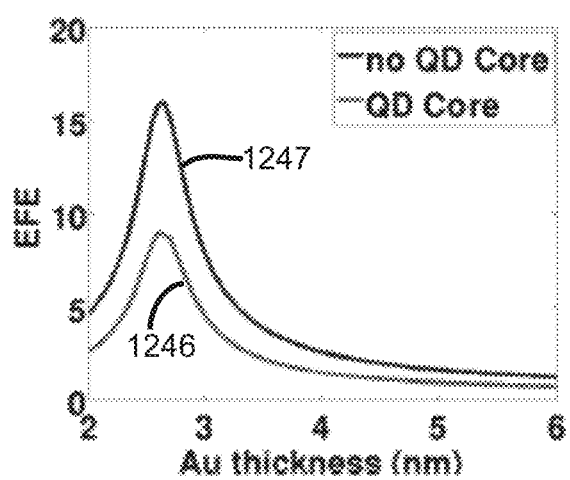
FIG. 12 shows the electric field enhancements as a function of gold thickness with and without a quantum dot core fur a silica radius equal to 20 nanometers, in accordance with various embodiments.

FIG. 10 shows the EFE at the center of a SA structure for various radii and thicknesses. The decreased maximum enhancement for larger core radii when using VSH does not appear when using the quasistatic model. FIG. 11 shows the EFE at the center of the QSA structure for various radii and thicknesses. As shown in FIG. 10, for a gold shell thickness of 3 nm, the maximum EFE is 14 for the SA structure at 800 nm wavelength excitation. As shown in FIG. 11, for a gold shell thickness of 3 nm, the maximum EFE is about 9 in the QSA structure at 800 nm wavelength excitation, for a silica radius of around 23 nm, showing the reduction due to the presence of the QD core. The EFE of the QSA nanoparticle can still result in a TPAF enhancement of greater than 2400. This reduction in EFE is also apparent in FIG. 12, which plots the EFE as a function of the gold layer thickness for a fixed silica radius of 20 nm, with (curve 1246) and without (curve 1247) a QD core.

Figure 13:
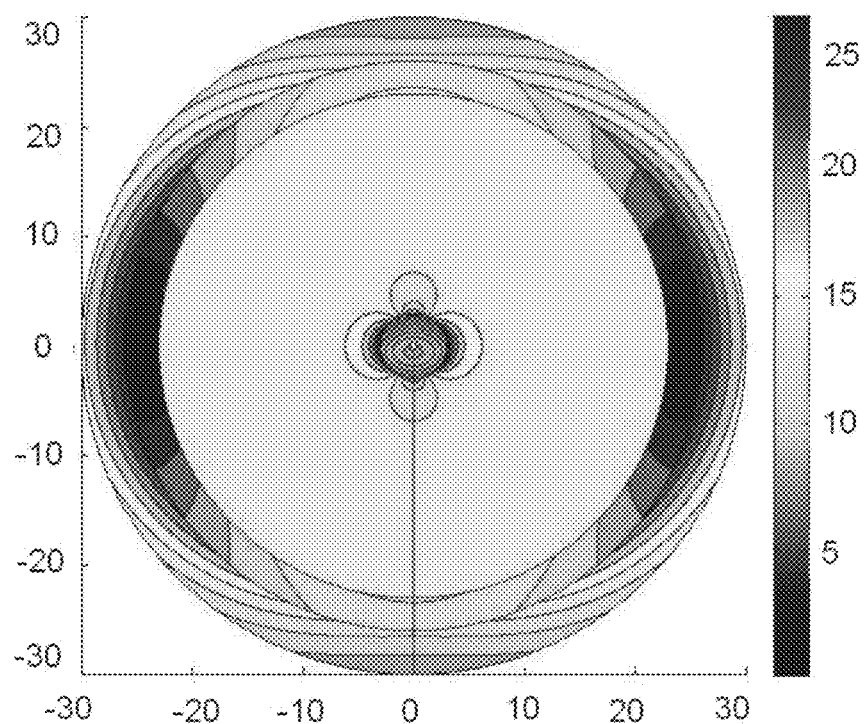
FIG. 13 shows spatial electric field enhancements of a quantum dot/silica/gold nanoparticle, in accordance with various embodiments.

FIG. 13 shows a spatial plot of a QD core-$SiO_2$-Au nanoparticle. The computed EFE in FIG. 13 was for a 3 nm radius QD, 20 nm thick $SiO_2$, and a 3 nm thick gold shell. The EFE in FIG. 13 is about 9 inside the QD core and is greater than 20 just outside the QD core, which is higher than the enhancement at the center of the SA particle of the same size.

The article, "Enhancement of Two-Photon Absorption-Induced florescence in semiconductor quantum dots by gold nanoparticles," L. Wang, a Ankuciwiez, J. Chen, and R. K. Jain in "Nonlinear Optics: Materials, Fundamentals and Applications," (Optical Society of America, 2009), p. NME4, discussed measurements providing a 10× improvement in TPAF of QDs in proximity to gold nanoparticles. In the dissertation of L. Wang, "Nonlinear optics in quantum-confined and surface-plasmon structures," Dissertation, May 2010, Univ. of New Mexico, https://repository.unm.edu/handle/1928/10916 (2010), theoretical field enhancement of 50 for 800 nm excitation in a core shell structure was demonstrated. The dissertation also included calculated field enhancements of approximately 50 to 100 at various wavelengths for a gold shell of 5 nm thickness surrounding a $SiO_2$ core of 15 nm radius, using finite integration techniques. Theoretical field enhancements for SiO2 core/Au shell nanoparticles using a quasistatic model with a size dependent loss in the ultrathin Au nanoshell have recently been shown in "Nanocomposite plasmonic fluorescence emitters with core/shell configurations," X. Miao, I. Brener, and T. S. Luk, Journal of the Optical Society of America B Optical Physics 27, 1561-1570 (2010). This modeling shows reduced field enhancement for thinner gold shells due to decreased electron mean free path and thus increased loss in the gold, but the enhancement increases to the bulk quasistatic model value for larger shell thicknesses. For thicker shells, the gold has the bulk dielectric constant and the enhancement is only dependent on the ratio of core radius to outer radius according to the quasistatic approximation. The lack of attenuation for thicker shells does not seem physically plausible. VSH analysis was used for a SiO2/Ag SA structure in the article, "Spectral properties of a fluorescing molecule within a spherical metallic nanocavity," J. Enderlein, Phys. Chem. Chem. Phys. 4, no. 12 (5): 2780-2786 (2002), which showed maximum enhancement on the order of 17 (450 nm wavelength) for a single shell thickness of 5 nm in a plot of wavelengths vs. core radii. Neither the effect of gold shell thickness on EFE, dielectric layer permittivity effect on EFE, multiple metal shells effect on EFE nor the effect of a QD at the center of the structure were considered in this article.

In the article, "Plasmonic effect of nanoshelled nanocavity on encapsulated emitter's spontaneous emission," J. Liaw and C. Liu, Journal of Quantitative Spectroscopy and Radiative Transfer 112, 2480-2485 (2011), an analysis included averaging the fluorescence enhancement over all positions and orientations of a dipole in the silica core having a gold or silver nanoshell. In the article, increased enhancement factors for thinner shells were noted, and a determination of the radiation efficiency factor (REF) was presented. This REF included the effect of the nanoshell on the far field radiation of the dipole, as well as the EFE, and is the ratio of far field fluorescent radiation intensity of the dipole fluorophore in a nanoshell to the fluorophore without a nanoshell. In the article, an analysis of a silica core with a silver or gold nanoshell was presented, for two shell thicknesses, 5 and 10 nm, and a maximum REF of 120 was obtained for a wavelength of 775 nm, a 40 nm radius silica core, and a 5 nm thick silver nanoshell. Since REF is a ratio of intensities, this corresponds to an EFE of approximately 11. The maximum REF for gold at a wavelength of 820 nm was 40 for a 40 nm radius silica core and 5 nm thick nanoshell. The REF of 40 corresponds to an EFE of approximately 6.3.

In the article, "Plasmonics quenching and enhancement of a fluorescing molecule outside and inside a silver metallic nanoshell," S. J. Norton and T. Vo-Dinh, IEEE Transactions on Nanotechnology (2011), an analysis of the fluorescence enhancement for a radially oriented dipole at various radii inside and outside a silver nanoshell with free space core and surrounding media was provided. The maximum EFE obtained was 5.5 for an inner radius of 45 nm and an outer radius of 50 nm at a 600 nm excitation wavelength. This low value compared to analysis, associated with embodiments taught herein, may be due to the free space permittivity of the core, the size dependent silver permittivity, which has increased loss, and the limited range of core radii and shell thicknesses considered. In various embodiments, structures may be provided that maximize the EFE for a nanoshelled structure over a wide range of metal nanoshell thicknesses, variations in the dielectric layer permittivity, and with a QD at the center.

In the article, "Multilayered metal core-shell nanostructures for inducing a large and tunable local optical field," H. Xu, Physical Review B 72, 073405 (2005), an analysis was presented that used Mie theory to analyze alternating silica-silver shelled structures in a vacuum media with a silver core. A calculation was presented that included a $1.2 \times 10^5$ intensity enhancement in the 1 nm thick innermost silica shell for a structure with a silver core and 4 alternating silica-silver shells in a vacuum media. The 1 nm silica layer may be too thin for a quantum dot, and may result in significant quenching of the fluorophore due to its proximity to the metal layers. In addition, it may be difficult to fabricate reliably. In various embodiments, structures may provide improved EFE in an alternate multilayered structure.

In the article, "Optimally designed nanolayered metal-dielectric particles as probes for massively multiplexed and ultrasensitive molecular assays," A. K. Kodali, X. Llora, and R. Bhargava, Proceedings of the National Academy of Sciences (2010), a discussion was presented regarding an analysis that optimizes field enhancement in multiple dielectric-metal layers. The discussion included designed optimal alternating silver-silica multi-shelled nanoparticles with silver cores that were optimized for field enhancement inside the inner dielectric layer. Reporter molecules in this dielectric have enhanced surface enhanced Raman scattering (SERS) spectra to facilitate detection of the nanoparticle. The article presented calculation of a net enhancement factor of $1 \times 10^{12}$ for alternating nanoparticles with 5 metal layers which corresponds to a $1 \times 10^3$ EFE. However, it is not clear how the minimum layer thickness is constrained in the optimization presented. As previously noted, without such a constraint, the field enhancement increases for smaller layer thicknesses.

Field enhancement factors in concentric shells can be calculated using $$E^i = \sum_{m,n} a^i_{nm} M^r_{nm} + b^i_{nm} N^r_{nm} + c^i_{nm} M_{nm} + d^i_{mn} N_{nm}$$

The electric field distribution inside each layer can be expressed most conveniently as a sum of VSHs, where n is the angular momentum, and m is its projection onto the z axis. In the model, the innermost layer may only include the two harmonics that are nonsingular (superscript "r") at the origin. At the outer layer, the incoming plane wave determines the coefficients for the incoming harmonics. There are two unknown coefficients for the harmonics that satisfy the radiation condition. The boundary conditions between layers can be used to calculate the coefficients of the VSHs. The quantum dot can be modeled as a dielectric material with an appropriate dielectric constant.

Figure 14:
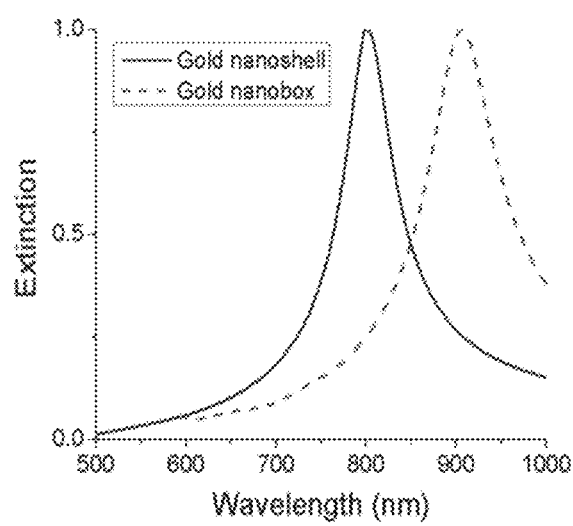
FIG. 14 shows excitation as a function of wavelength for a gold nanoshell and a gold hollow nanobox, in accordance with various embodiments.

A concentric shell plasmonic QD can include a QD core encased by a dielectric shell that is encased by a metal nanoshell as shown in FIG. 1. The band-edge electron mean free path in gold is 57 nm, which can be much greater than (>>) the thickness of a gold nanoshell. Some electrons may oscillate freely along with an external oscillating electric field. Strong resonant enhancements of the electric field can occur. These resonant enhancements depend on the shell diameter, thickness, and excitation wavelength. FIG. 14 shows excitation as a function of wavelength for a gold nanoshell and a gold hollow nanobox. The resonance in a gold nanoshell is shown for an outer radius $r_{out}$=10 nm and an inner radius $r_{in}$=8.8 nm. The resonance in a gold hollow nanobox is shown for an edge length=20 nm and a wall thickness=1.2 nm.

Figure 15:
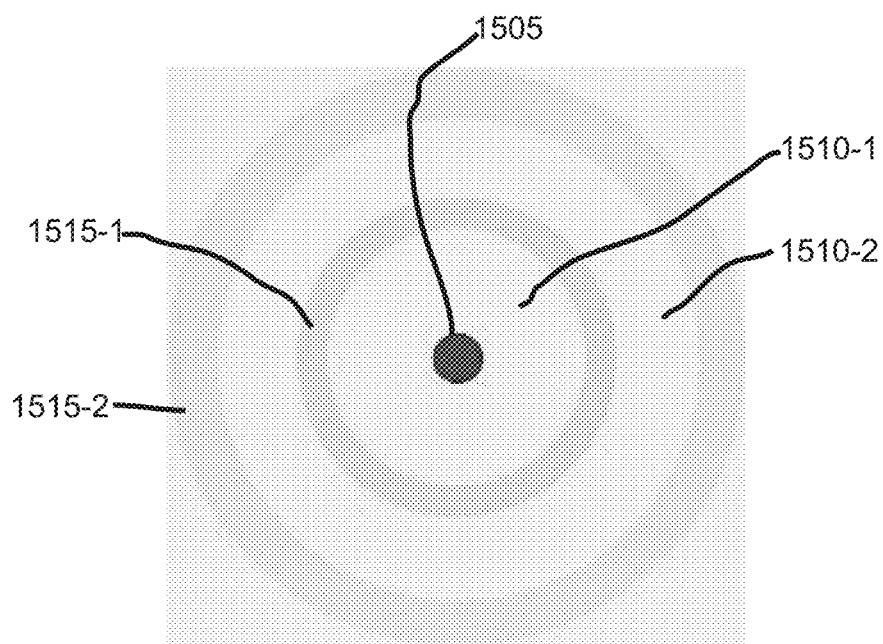
FIG. 15 shows an example multi-shelled nanostructure, in accordance with various embodiments.
Figure 16:
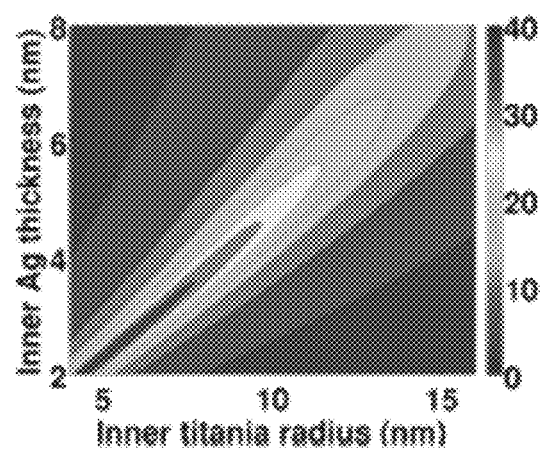
FIG. 16 shows electric field enhancements for the multi-shelled nanostructure of FIG. 15 consisting of a given set of materials as a function of the inner layer thicknesses, in accordance with various embodiments.

FIG. 15 shows an example embodiment of a multi-shelled nanostructure (MSN). The MSN includes a light-absorbing and light-emitting core 1505, a dielectric 1510-1 enclosing light-absorbing and light-emitting core 1505, and a conductive nanoshell 1515-1 enclosing dielectric 1510-1 and light-absorbing and light-emitting core 1505. Additionally, dielectric 1510-2 encloses conductive nanoshell 1515-1 and is enclosed by conductive nanoshell 1515-2. To consider the improved EFE for high relative permittivity dielectrics discussed herein, the EFE in the core of the MSN shown in FIG. 15 was considered for a titania dielectric layer having a relative permittivity of about 6.2. This structure was analyzed at an excitation wavelength of 800 nm. The EFE for this structure with an 80 nm outer diameter titania and an 8 nm thick Ag outer shell is shown in FIG. 16, showing enhancements over 40. The EFE for the metal double shell is shown for varying inner layers. As in the case of the silica nanostructure in FIG. 11, the maximum EFE increases with small layer thicknesses. However, even for an inner gold layer as large as 6 nm, the maximum EFE is 23.

Figure 17:
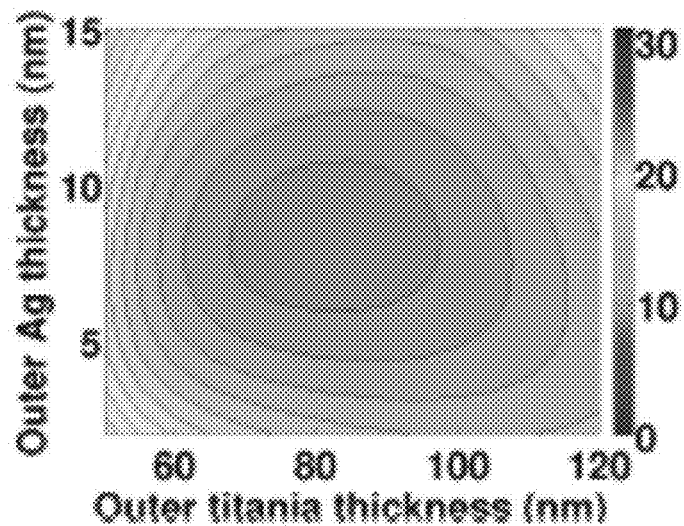
FIG. 17 shows electric field enhancements fur the multi-shelled nanostructure of FIG. 15 consisting of a given set of materials as a function of the outer layer thicknesses, in accordance with various embodiments.
Figure 18:
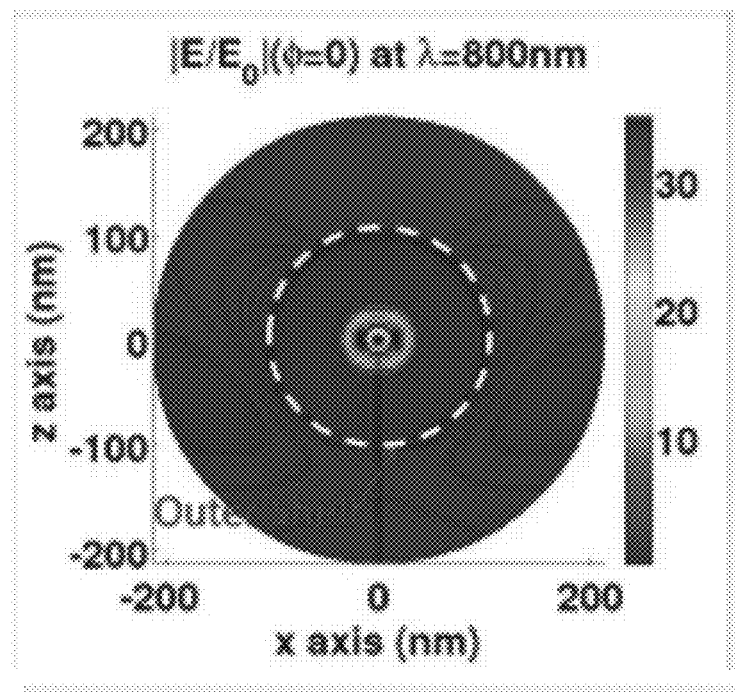
FIG. 18 shows spatial electric field enhancements fur the multi-shelled nanostructure of FIG. 15 optimized in material parameters from analysis associated with FIGS. 15-17, in accordance with various embodiments.
Figure 19:
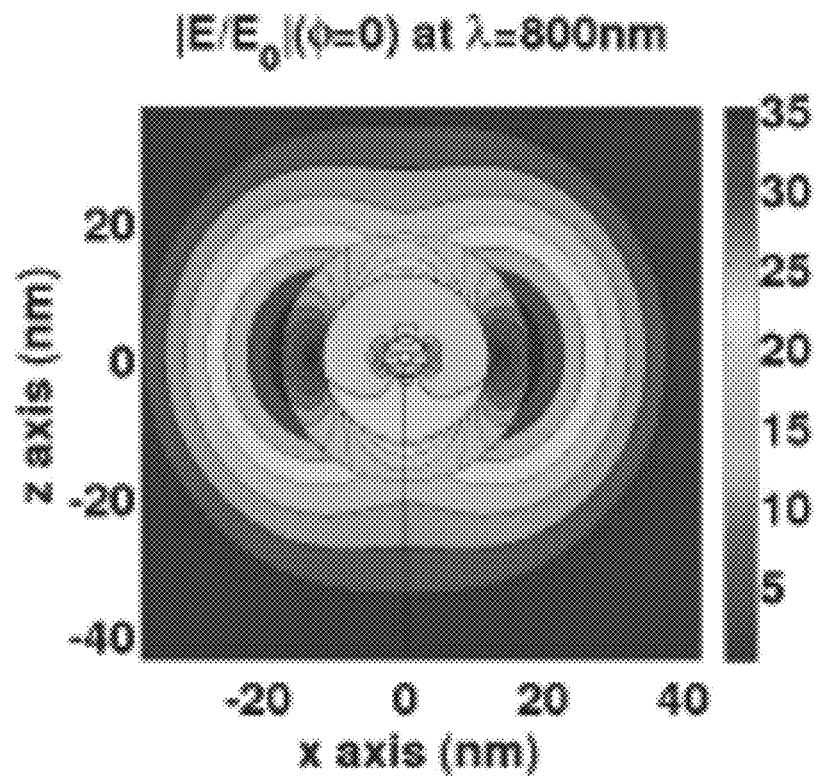
FIG. 19 shows magnified spatial electric field enhancements for the double shelled nanoparticle of FIG. 18, in accordance with various embodiments.

FIG. 17 shows electric field enhancements for the multi-shelled nanostructure of FIG. 15 consisting of a given set of materials as a function of the outer layer thicknesses. FIG. 17 shows the EFE for a 6 nm thick inner silver layer and 12 nm radius inner titania layer as a function of the outer layer thicknesses. The maximum EFE structure found has a 12 nm radius inner titania layer, 6 nm thick inner Ag shell, 80 nm thick outer titania layer, and an outer Ag shell of 8 nm thickness. The EFE of this structure is 23 in the core, which can result in a TPAF enhancement of 160,000 for the QD in the core. A spatial field enhancement plot of this optimal structure is shown in FIG. 18 and a zoomed-in plot for the inner layers in FIG. 19.

It is also noted that double-shelled QD/TiO$_2$/Au/TiO$_2$/Au nanoparticles may lead to an estimated TPAF greater than 160,000 relative to the same QD. However, increased losses estimated from the measured permittivity of ultrathin gold films, less than 7 nm thick, may result in greatly reduced EFE for QD/SiO$_2$/Au. nanoparticles. Estimation and comparison of the fluorescent quantum yield of various fluorophore and nanostructure configurations may be provided by examining the effects of advanced nanostructures on the emission of fluorophores in the far field.

In the article, "Plasmonic fluorescent quantum dots," Y. Jin and X. Gao, Nat Nano 4, 571-576 (2009), the synthesis of a QD core in a 3-5 nm thick polymer shell in a 2-3 nm gold shell was reported. A quantum yield of 39% was measured. The quantum yield can be improved by changing the polymer and gold shell thicknesses and conducting a synthesis of thin shells corresponding to the greatest EFE obtained in the models presented herein, as seen in FIGS. 2-5.

The article, "On the incorporation mechanism of hydrophobic quantum dots in silica spheres by a reverse microemulsion method," R. Kook, M, M. van Schooneveld, J. Hilhorst, C. de Mello Doneg, D. C. 't Hart, A. van Blaaderen, D. Vanmaekelbergh, and A. Meijerink, Chemistry of Materials 20, 2503-2512 (2008), is incorporated by reference in its entirety. In this article, a method was presented that uses reverse microemulsion, where a QD, tetraethylorthosilicate, and ammonia localize to reverse micelles resulting in the growth of a silica layer on the QD. The article, "Preparation, characterization, and optical properties of gold, silver, and Gold-Silver alloy nanoshells having silica cores," J. Kim, W. W. Bryan, and T. R. Lee, Langmuir 24, 11147-11152. (2008), is incorporated by reference in its entirety. In this article, a method was presented that grows a gold nanoshell on silica nanoparticles by first attaching gold nanoparticles to the surface of the silica using aminopropyltrimethoxysilane. The gold nanoparticles are subsequently used to nucleate the growth of a complete gold shell.

In an embodiment, a multi-shelled nanostructure may be fabricated by using reverse microemulsion to grow a dielectric layer on a QD followed by attaching conductive nanoparticles to the formed dielectric layer and using the attached nanoparticles to nucleate the growth of a complete conductive shell on the dielectric layer. Repeated formation of a dielectric layer followed by attaching conductive nanoparticles to the formed dielectric layer to nucleate a complete subsequent conductive shell on a subsequent dielectric layer can result in a multi-shelled nanostructure with any number of dielectric shells followed by conductive shells. For example, reverse microemulsion can be used to grow a silica layer on a QD.

Figure 20A:
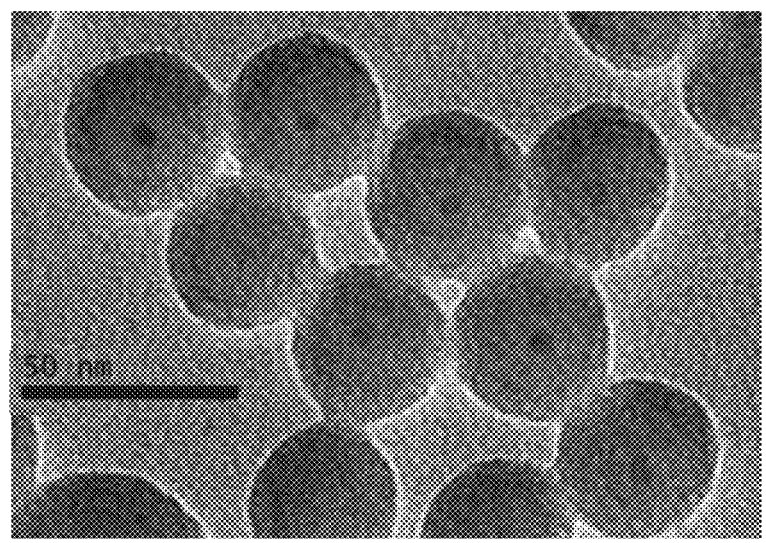
FIG. 20A shows synthesized silica coated quantum dots that can be processed into a double metal shell, in accordance with various embodiments.
Figure 20B:
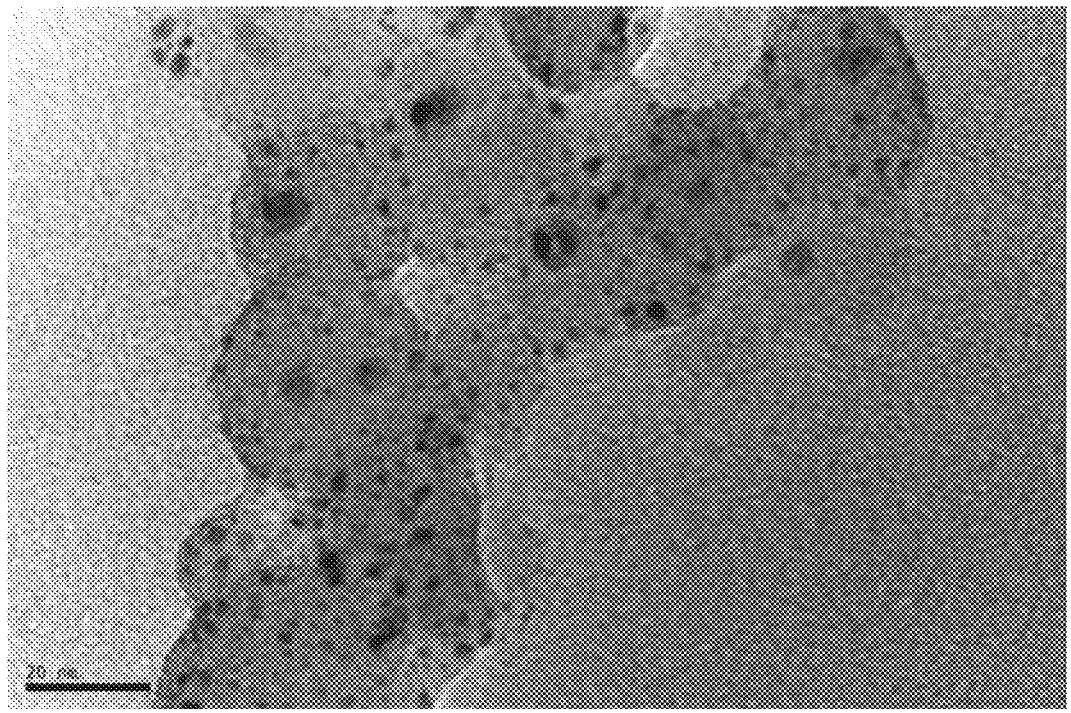
FIG. 20B shows silica coated quantum dots of FIG. 18A with gold seed on their surface, in accordance with various embodiments.

FIG. 20A shows a transmission electron microscopy (TEM) image of the silica coated QDs, where spheres with less than 40 nm diameter and a dark core can be seen. The silica nanosphere is gold coated with gold nanoparticles to nucleate a complete gold nanoshell on the silica nanosphere in order to fabricate a QD/silica shell/gold shell/silica shell/gold shell nanostructure. FIG. 20B shows silica-coated QDs with gold seed on their surface, where gold shells of thickness less than 3 nm can be grown on these seeded nanoparticles. Using gold nanoparticles as nucleation sites on a silica nanosphere may be accompanied by problems with agglomeration of the nanoparticles when gold coating silica coated QDs. Other researchers have also report problems with agglomeration when synthesizing nanoshells on less than 100 nm diameter silica nanospheres.

Though bulk dielectric constants of gold and silver have been used in example modeling herein, permittivity of ultra thin layers of noble metals may be appropriate. It is noted that the size dependent dielectric of gold film thicknesses, reported in an article, has an increased imaginary component, which would result in increased loss and reduced EFE. The gold films in this study were discontinuous at a thickness of 3 nm, so additional experiments may be needed to determine how different fabrication methods affect permittivity. In an article, a review of previously proposed surface scattering based estimates of the changes in metal permittivity due to size dependent modification to the electron mean free path was presented. The analysis in the article demonstrated that, among these models, the billiard or Lambertian scattering models are most consistent with the experimental results reported in another article, and these models also fit the mean free path obtained from the quantum mechanical analysis by other researchers.

For photodynamic therapy, the energy from two photon absorption in the QD must be nonradiatively transferred to a photosensitizing molecule on the surface of the NP. The efficiency of this nonradiative energy transfer along with the radiation efficiency from the QD to the far field for estimating the fluorescence efficiency may be the subject of a subsequent publication.

In an example, with shells fabricated with a dielectric constant close to that of bulk gold, then a 100 nm radius of a MSN, as discussed herein, may enable a TPAF signal enhancement of greater than 160,000. The shells around the QD core may also result in reduced toxicity, allowing these nanoparticles to be used for biomedical applications such deep tissue imaging. In an example, the minimum shell thickness in the MSN can be 6 nm. Smaller core and thinner shell nanoparticles may lead to larger TPAF signal enhancements.

Figure 21:
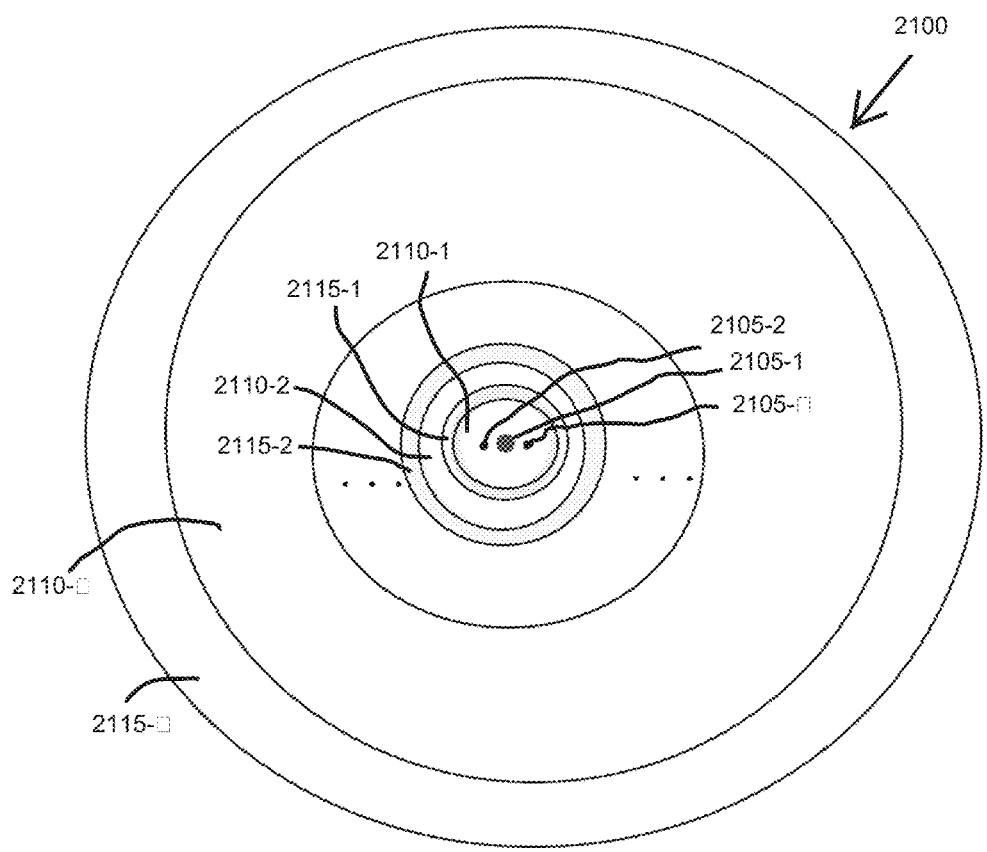
FIG. 21 shows a multi-shelled nanostructure, in accordance with various embodiments.

FIG. 21 shows an example embodiment of a multi-shelled nanostructure 2100. Nanostructure 2100 can include one or more light-absorbing and light-emitting cores 2105-1, 2105-2 . . . 2105-N enclosed within a conductive nanoshell 2115-1 and separated from the conductive nanoshell 2115-1 by a dielectric 2110-1, where conductive nanoshell 2115-2 encloses nanoshell 2115-1 and is separated from nanoshell 2115-1 by dielectric 2110-2. Enclosed can be also be referred to as encased or encapsulated. Separating each conductive nanoshell 2115-1 . . . 2115-M in the multi-shelled nanostructure 900 is a dielectric 2110-1 . . . 2110-M, respectively. It can be seen that multi-shelled nanostructure 2100 can be structured with one or more light-absorbing and tight-emitting cores enclosed within one or more nested conductive nanoshells. The nested conductive nanoshells can be, but not limited to, concentric conductive nanoshells, such as concentric portions of spheres. The one or more light-absorbing and light-emitting cores 2105-1 . . . 2105-N are separated from innermost nanoshell 2115-1 by dielectric 2110-1. A dielectric can be disposed between every pair of adjacent nanoshells 2115-1 . . . 2115-M, where each of nanoshells 2115-1 . . . 2115-M is a conductive nanoshell.

The nanosized structures can be realized in different structural formats. The nanosized structures can be generally spherical (e.g., nanoparticle) or cylindrical (e.g., nanowire) in shape, with the light-absorbing and light-emitting core(s) located generally at the center of the nanoparticle or nanowire. The number of concentric/nested nanoshells is unlimited, in principle; but, in practice, typically ranges from 1 to 10 nanoshells; and most typically from 2 to 4 nanoshells. The total outer diameter of the nanoparticle or nanowire can range from 10 nm to 900 nm, typically ranging from 20 nm to 100 nm.

Light-absorbing and light-emitting cores 2105-1, 2105-2 . . . 2105-N can include, but are not limited to, organic luminophores, fluorophores, non-toxic fluorophores, semiconductor quantum dots (SQDs), or combinations thereof. The organic luminophores can include fluorescent dyes such as Rhodamine 6G. The SQDs can include, but are not limited to, CdSe, CdS, CdTe, InAr, InP, CuS, CuSe, GeTe, PbSe, CdSeS, or combinations thereof. The diameter of a light-absorbing and light-emitting core, such as a QD, can range from 0.1 nm to 100 nm, typically ranging from 5 to 20 nm.

Dielectrics 2110-1 . . . 2110-M can include, but are not limited to, a low-loss high-index dielectric material, silica ($SiO_2$), titania ($TiO_2$), alumina ($Al_2O_3$), ZnS, $Si_3N_4$, GaN, or combinations thereof Selected ones of dielectrics 2110-1 . . . 2110-M can be composed of different materials from selected other ones of dielectrics 2110-1 . . . 2110-M. The thickness of a dielectric insulating layer can range from 1 nm to 300 nm, typically ranging from 5 to 30 nm. One or more of dielectrics 2110-1 . . . 2110-M can be solid or porous.

Conductive nanoshells 2115-1 . . . 2115-M can include, but are not limited to, a metallic layer, a plasmonic noble metal, Au, Ag, Pt, a binary alloy of Au and Ag, or combinations thereof. Selected ones of conductive nanoshells 2115-1 . . . 2115-M can be composed of different materials from selected other ones of conductive nanoshells 2115-1 . . . 2115-M. The thickness of a conductive nanoshell can range from 1 nm to 100 nm; range from 1 to 30 nm; or range from 1 to 10 nm. One or more of conductive nanoshells 2115-1 . . . 2115-M can be continuous or discontinuous, textured, patterned, filagreed, or have holes through the thickness.

Figure 22:
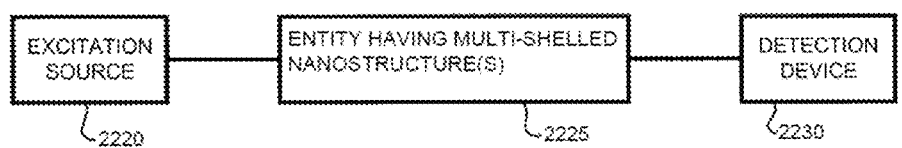
FIG. 22 shows an example embodiment of an arrangement using a multi-shelled nanostructure, in accordance with various embodiments.

FIG. 22 shows an example embodiment of an arrangement 2200 using a multi-shelled nanostructure. Arrangement 2200 includes an excitation source 2220, an entity 2225 associated with one or more multi-shelled nanostructures, and a detection device 2230. Entity 2225 may be, but is not limited to, a biological entity. Excitation source 2220 can include, among other sources, a light source such as a laser. Excitation source 2220 can be implemented using a light source with associated optical elements to focus, steer, or wavelength shift output from the light source. The one or more multi-shelled nanostructures associated with entity 2225 can be realized similar to or identical to one of more multi-shelled nanostructure as taught herein. Excitation source 2220 can be selected based on the characteristics of the multi-shelled nanostructures. Alternatively, the multi-shelled nanostructures can he selected based on the characteristics of the light source. The selection of excitation source 2220 and the multi-shelled nanostructures can be made considering characteristics of both the excitation source 2220 and the multi-shelled nanostructure in view of the application for which they are to be applied.

Detection device 2230 can include imaging components. Such components can include fitters to separate light generated by the multi-shelled nanostructures in response to excitation light from an appropriate excitation source 2220 from light from the appropriate excitation source 2220 reflected from entity 2225 and the multi-shelled nanostructures. In addition, filters can be used to separate a number of signals that are generated by the multi-shelled nanostructures or the multi-shelled nanostructures in combination with other elements for measuring characteristics of entity 2225. Detection device 2230 can include data collection equipment such as imaging camera or various types of spectrographic equipment.

Figure 23:
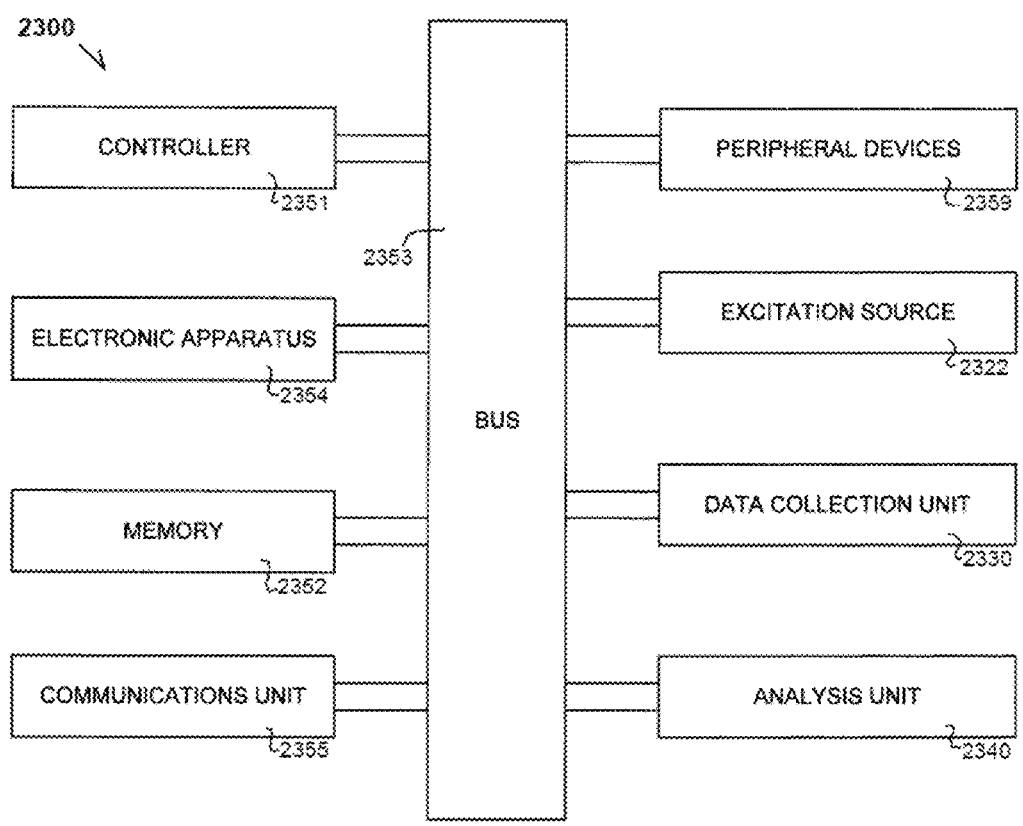
FIG. 23 depicts a block diagram of features of an example embodiment of a system arranged to manage multi-shelled nanostructures associated with determining characteristics of an entity, in accordance with various embodiments.

FIG. 23 depicts a block diagram of features of an example embodiment of a system 2300 arranged to manage multi-shelled nanostructures associated with determining and/or modifying characteristics of an entity. System 2300 includes a data collection unit 2330 and components to conduct analysis of data acquired by data collection unit 2330. Data collection unit 2330 can be arranged to include optical sensing components to receive signals from multi-shelled nanostructures excited by excitation source 2322. Optical sensing components can include one or more filters to separate the responses from exciting the entity and the multi-shelled nanostructures Excitation source 2322 can include, but is not limited to, a laser. Multi-shelled nanostructures can be structured in accordance with the teachings herein.

System 2300 can include a controller 2351, a memory 2352, an electronic apparatus 2354, and a communications unit 2355. Controller 2351, memory 2352, and communications unit 2355 can be arranged to operate as a processing unit to control management of data collection unit 2330 and analysis of data collected by data collection unit 2330 and to perform operations on data signals used to control excitation source 2322 to excite the entity, the associated multi-shelled nanostructures, or both the entity and the associated multi-shelled nanostructures. An analysis unit can be distributed among the components of system 2300 including electronic apparatus 2354. Alternatively, system 2300 can include an analysis unit 2340 to manage the analysis of data collected. Analysis unit 2340 may also include one or more machine-readable memory devices.

System 2300 can also include a bus 2353, where bus 2353 provides electrical conductivity among the components of system 2300. Bus 2353 can include an address bus, a data bus, and a control bus, each may be independently configured. Bus 2353 can be realized using a number of different communication mediums that allows for the distribution of components of system 2300 Use of bus 2353 can be regulated by controller 2351.

In various embodiments, peripheral devices 2359 can include displays, additional storage memory, and/or other control devices that may operate in conjunction with controller 2351 and/or memory 2352. In an embodiment, controller 2351 can be realized as a processor or a group of processors that may operate independently depending on an assigned function. Peripheral devices 2359 can include a display, which may be arranged as a distributed component, that can be used with instructions stored in memory 2352 to implement a user interface to manage the operation of data collection unit 2330, analysis unit 2340, and/or components distributed within system 2300. Such a user interface can be operated in conjunction with communications unit 2355 and bus 2353.

Figure 24:
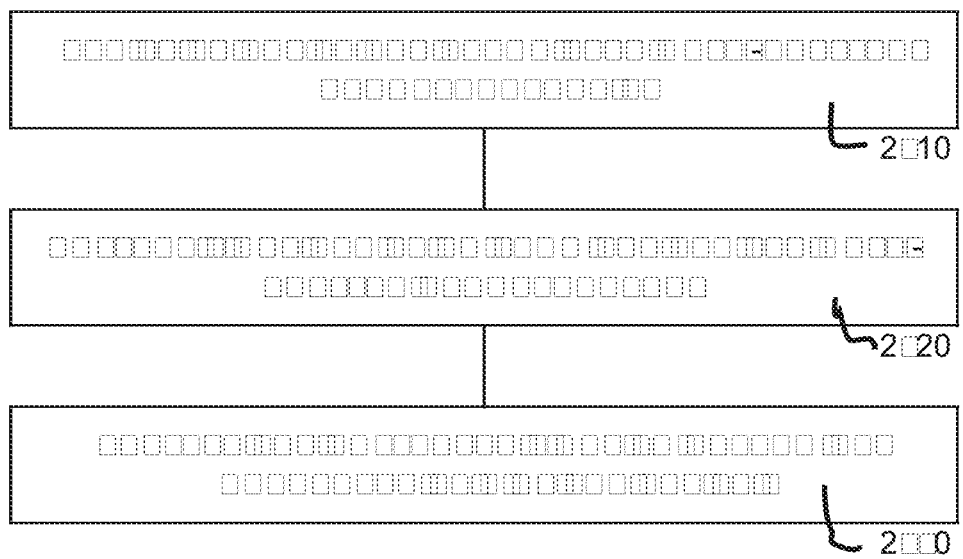
FIG. 24 shows features of an example embodiment of a method of using multi-shelled nanostructures, in accordance with various embodiments.

FIG. 24 shows features of an example embodiment of a method of using multi-shelled nanostructures. At 2410, an entity and an associated multi-shelled nanostructure are excited. The multi-shelled nanostructure can be realized by a multi-shelled nanostructure similar to or identical to multi-shelled nanostructures as taught herein. The multi-shelled nanostructure can include a quantum dot, an innermost insulating material surrounding the quantum dot, an innermost metallic material substantially enclosing the quantum dot and the innermost insulating material, an outermost dielectric substantially enclosing the innermost metallic material, and an outermost metallic material substantially enclosing the outermost dielectric. Exciting the entity and the associated multi-shelled nanostructure can include exciting the entity and a number of associated multi-shelled nanostructures. Exciting the entity and the associated multi-shelled nanostructure can include applying a nonlinear excitation. The applied nonlinear excitation can have a wavelength of about 800 nanometers. Nonlinear excitations at other wavelengths can be used. Applying the nonlinear excitation can include using a laser. The entity can be a biological entity.

At 2420, light radiating from the excited multi-shelled nanostructure(s) is collected. The light is different from the excitation of the entity and the associated multi-shelled nanostructure(s). At 2430, the collected light can be analyzed using a processing unit to determine characteristic of the entity from the analyzed collected light. Analyzing the collected light can include deep-tissue imaging of a biological entity.

In various embodiments, a method using multi-shelled nanostructures can include functionalizing the multi-shelled nanostructures with biomolecules to generate cytotoxic reactive oxygen species in a biological entity by two-photon absorption-induced fluorescence. Exciting the multi-shelled nanostructures can be conducted at a wavelength and intensity to cause increased accumulation of cytotoxic reactive oxygen species in target tissue of the biological entity. Exciting the multi-shelled nanostructures can be conducted at a wavelength and intensity to cause selective destruction of malignant cells in target tissue of the biological entity.

Multi-shelled nanostructures, structured in a similar or identical arrangement as taught herein, can be used in a variety of applications. These multi-shelled nanostructures can be excited by electromagnetic radiation for analysis and/or as a modifying tool. The excitation can be conducted at a wavelength in a range from about 600 nm to about 1300 nm. Other wavelengths may be used. Exciting the multi-shelled nanostructures by electromagnetic radiation can be conducted at a wavelength selected for a given application. In addition, choice of one or more light-absorbing and light-emitting cores in the fabrication of the multi-shelled nanostructures can be made for operation based the selected wavelength. The one or more light-absorbing and light-emitting cores can be selected from a number of different structures, as discussed herein, including but not limited to one or more quantum dots.

Although specific embodiments have been illustrated and described herein, it will be appreciated by those of ordinary skill in the art that any arrangement that is calculated to achieve the same purpose may be substituted for the specific embodiments shown. Upon studying the disclosure, it will be apparent to those skilled in the art that various modifications and variations can be made in the devices and methods of various embodiments of the invention. Various embodiments can use permutations and/or combinations of embodiments described herein. Other embodiments will be apparent to those skilled in the art from consideration of the specification and practice of the embodiments disclosed herein. It is to be understood that the above description is intended to be illustrative, and not restrictive, and that the phraseology or terminology employed herein is for the purpose of description.

What is claimed is:

1. An apparatus comprising:
    a single core consisting of a single light-absorbing and light-emitting structure;
    an inner dielectric layer composed of one or more dielectric materials enclosing and contacting the single core;
    an innermost nanoshell enclosing the inner dielectric layer and the single core, the innermost nanoshell being a conductive nanoshell, the innermost nanoshell and the inner dielectric layer arranged such that the inner dielectric layer prevents direct contact of the single core with the innermost nanoshell;
    an outer dielectric disposed enclosing the innermost nanoshell; and
    an outermost nanoshell enclosing the outer dielectric, the outermost nanoshell being a conductive nanoshell.

2. The apparatus of claim 1, wherein the apparatus includes one or more additional conductive nanoshells enclosing the inner dielectric layer and the single core. the one or more additional conductive nanoshells enclosed by the outer insulating dielectric and the outermost nanoshell, each conductive nanoshell separated from an adjacent conductive nanoshell by a dielectric.

3. The apparatus of claim 2, wherein one or more of the conductive nanoshells have a structure that is continuous, textured, patterned, filigreed, or has holes.

4. The apparatus of claim 1, wherein the nanoshells are structured as concentric nested nanoshells.

5. The apparatus of claim 1, wherein the single core, the inner dielectric, the innermost nanoshell, the outer dielectric, and the outermost nanoshell are arranged having a spherical structure or a cylindrical structure.

6. The apparatus of claim 1, wherein the single core includes an organic luminophore, a fluorophore, a non-toxic fluorophore, or a semiconductor quantum dot.

7. The apparatus of claim 1, wherein the single core includes one quantum dot selected from one of CdSe, CdS, CdTe, InAs, InP, CuS, CuSe, GeTe, PbSe, or CdSeS quantum dots or a composite material quantum dot consisting of two or more of CdSe CdS, CdTe, InAs, InP, CuS, CuSe, GeTe, PbSe, or CdSeS.

8. The apparatus of claim 1, wherein the inner dielectric includes one or more of silica, titania, alumina, ZnS, $Si_3N_4$, or GaN.

9. The apparatus of claim 1, wherein the inner dielectric is porous.

10. The apparatus of claim 1, wherein the outermost nanoshell includes a plasmonic noble metal.

11. The apparatus of claim 1, wherein the outermost nanoshell includes a metal.

12. The apparatus of claim 1, wherein the innermost nanoshell has a material composition different from that of the outermost nanoshell.

13. The apparatus of claim 1, wherein the inner dielectric has a material composition different from that of the outer dielectric.

14. The apparatus of claim 1, wherein the single core has a diameter in the range from 0.5 nm to 2 nm.

15. The apparatus of claim 1, wherein the single light-absorbing and light-emitting structure of the single core is selected such that light-emitting in response to an excitation is an up conversion process.

16. The apparatus of claim 1, wherein the single light-absorbing and light-emitting structure of the single core is a semiconductor quantum dot composed of multiple materials.

17. The apparatus of claim 1, wherein each of the innermost nanoshell, and the outermost nanoshell have a thickness less than 10 nm.

18. The apparatus of claim 1, wherein each of the innermost nanoshell, and the outermost nanoshell have a thickness less than 6 nm.

19. A method comprising:
    forming a single core consisting of a single light-absorbing and light-emitting structure cores;
    forming an inner dielectric layer composed of one or more dielectric materials enclosing and contacting the single core;
    forming an innermost nanoshell enclosing the inner dielectric and the single core, the innermost nanoshell being a conductive nanoshell, the innermost nanoshell and the inner dielectric layer arranged such that the inner dielectric layer prevents direct contact of the single core with the innermost nanoshell;
    forming an outer dielectric disposed enclosing the innermost nanoshell; and
    forming an outermost nanoshell enclosing the outer dielectric, the outermost nanoshell being a conductive nanoshell.

20. The method of claim 19, wherein forming the single core includes forming a semiconductor or insulator quantum dot.

21. The method of claim 20, wherein forming the inner dielectric includes using reverse microemulsion to grow a dielectric layer on the quantum dot.

22. The method of claim 21, wherein the method includes attaching conductive nanoparticles to the formed dielectric and using the attached nanoparticles to nucleate growth of the complete innermost nanoshell on the dielectric.

23. The method of claim 21, wherein the method includes repeating formation of a dielectric followed by attaching conductive nanoparticles to the formed dielectric layer to nucleate complete subsequent conductive nanoshells on subsequent dielectrics, forming a multi-shelled nanostructure with a selected number of pairs of a dielectric followed by conductive nanoshell.

24. A method comprising:
exciting an entity and an associated multi-shelled nanostructure, the multi-shelled nanostructure including:
a single core consisting of a single light-absorbing and light-emitting structure;
an inner dielectric layer composed of one or more dielectric materials enclosing and contacting the single core;
an innermost nanoshell enclosing the inner dielectric layer and the single core, the innermost nanoshell being a conductive nanoshell, the innermost nanoshell and the inner dielectric layer arranged such that the inner dielectric layer prevents direct contact of the single core with the innermost nanoshell;
an outer dielectric disposed enclosing the innermost nanoshell; and
an outermost nanoshell enclosing the outer dielectric, the outermost nanoshell being a conductive nanoshell;
collecting light radiating from the excited multi-shelled nanostructure, the light being different from the excitation of the entity and associated multi-shelled nanostructure; and
analyzing the collected light using a processing unit to determine characteristic of the entity from the analyzed collected light.

25. The method of claim 24, wherein exciting the entity and the associated multi-shelled nanostructure includes applying a nonlinear excitation.

26. The method of claim 25, wherein applying the nonlinear excitation includes applying a nonlinear excitation having a wavelength of about 800 nanometers.

27. The method of claim 25, wherein applying the nonlinear excitation includes applying the nonlinear excitation using a laser.

28. The method of claim 24, wherein the entity is a biological entity.

29. The method of claim 28, wherein analyzing the collected light includes deep-tissue imaging of the biological entity.

30. The method of claim 28, wherein the method includes functionalizing the associated multi-shelled nanostructure and additional multi-shelled nanostructures with biomolecules to generate cytotoxic reactive oxygen species by two-photon absorption-induced fluorescence.

31. The method of claim 30, wherein the exciting is conducted at a wavelength and intensity to cause increased accumulation of cytotoxic reactive oxygen species in target tissue of the biological entity.

32. The method of claim 30, wherein the exciting is conducted at a wavelength and intensity to cause selective destruction of malignant cells in target tissue of the biological entity.

33. The method of claim 24, wherein the exciting is conducted at a wavelength in a range from about 600 nm to about 1300 nm.

34. The method of claim 24, wherein the single core includes a quantum dot.

35. An apparatus comprising:
an excitation source;
a multi-shelled nanostructure including:
a single core consisting of a single light-absorbing and light-emitting structure;
an inner dielectric layer composed of one or more dielectric materials enclosing and contacting the single core:
an innermost nanoshell enclosing the inner dielectric layer and the single core, the innermost nanoshell being a conductive nanoshell, the innermost nanoshell and the inner dielectric layer arranged such that the inner dielectric layer prevents direct contact of the single core with the innermost nanoshell;
an outer dielectric disposed enclosing the innermost nanoshell; and
an outermost nanoshell enclosing the outer dielectric, the outermost nanoshell being a conductive nanoshell; and
a detection device arranged to sense light emitted from the multi-shelled nanostructure in response to excitation of the multi-shelled nanostructure by the excitation source.

36. he apparatus of claim 35, wherein the multi-shelled nanostructure includes one or more additional conductive nanoshells enclosing the inner dielectric layer and the single core, the one or more additional conductive nanoshells enclosed by the outer insulating dielectric and the outermost nanoshell, each conductive nanoshell separated from an adjacent conductive nanoshell by a dielectric.

37. The apparatus of claim 35, wherein the nanoshells of the multi-shelled nanostructure are structured as concentric nested nanoshells.

38. The apparatus of claim 35, wherein the single core, the inner dielectric, the innermost nanoshell, the outer dielectric, and the outermost nanoshell are arranged having a spherical structure or a cylindrical structure.

39. The apparatus of claim 35, wherein the single core includes an organic luminophore, a fluorophore, a non-toxic fluorophore, or a semiconductor quantum dot.

40. The apparatus of claim 35, wherein the outermost nanoshell includes a plasmonic noble metal.

41. The apparatus of claim 35, wherein the innermost nanoshell has a material composition different from that of the outermost nanoshell.

42. The apparatus of claim 35, wherein the inner dielectric has a material composition different from that of the outer dielectric.

43. The apparatus of claim 35, wherein the excitation source includes one or more lasers whose input directions and wavelengths are identical or whose input directions and wavelengths are substantially different.

44. The apparatus of claim 35, wherein the detection device is arranged as a component of an imaging device.

45. The apparatus of claim 44, wherein the single light-absorbing and light-emitting structure of the single core is selected such that the light emitted in response to the excitation is up converted light.

* * * * *